United States Patent
Kirio et al.

[11] Patent Number: 5,990,161
[45] Date of Patent: Nov. 23, 1999

[54] HYDROXIMIC ACID DERIVATIVES

[75] Inventors: Yoshie Kirio; Takako Maeda; Norio Sasaki; Norishige Toshima; Nobumitsu Sawai; Bruce Milligan, all of Ibaraki, Japan; Joseph Perez; Jean-Pierre Vors, both of Lyons, France; Daniel B. Gant, Durham, N.C.

[73] Assignee: Rhone-Poulenc Agrochimie, Lyons, France

[21] Appl. No.: 09/222,870

[22] Filed: Dec. 30, 1998

Related U.S. Application Data

[62] Division of application No. 08/945,343, filed as application No. PCT/EP96/01386, Mar. 29, 1996.

[30] Foreign Application Priority Data

Apr. 17, 1995 [JP] Japan ........................ 7-90733
Jul. 27, 1995 [WO] WIPO ................... PCT/EP95/02984
Jul. 31, 1995 [JP] Japan ..................... 7-194670
Jan. 11, 1996 [WO] WIPO .................. PCT/IB96/00276

[51] Int. Cl.⁶ .................... A01N 37/52; A01N 33/24; C07C 251/26
[52] U.S. Cl. .............. 514/508; 558/7; 514/640
[58] Field of Search ............... 514/508, 640; 558/7

[56] References Cited

U.S. PATENT DOCUMENTS

| | | | |
|---|---|---|---|
| 5,104,872 | 4/1992 | Tsubata et al. | 514/238.2 |
| 5,194,662 | 3/1993 | Brand et al. | 560/35 |
| 5,268,488 | 12/1993 | Watanabe et al. | 548/561 |
| 5,292,759 | 3/1994 | Brand et al. | 514/339 |
| 5,332,752 | 7/1994 | Cliff et al. | 514/369 |
| 5,449,803 | 9/1995 | Watanabe et al. | 558/1 |
| 5,510,344 | 4/1996 | Cliff et al. | 514/212 |

FOREIGN PATENT DOCUMENTS

| | | |
|---|---|---|
| 0370629 | 5/1990 | European Pat. Off. |
| 01378308 | 7/1990 | European Pat. Off. |
| 0398692 | 11/1990 | European Pat. Off. |
| 0414153 | 2/1991 | European Pat. Off. |
| 0426460 | 5/1991 | European Pat. Off. |
| 0463488 | 1/1992 | European Pat. Off. |
| 0487409 | 5/1992 | European Pat. Off. |
| 0532022 | 3/1993 | European Pat. Off. |
| 0535928 | 4/1993 | European Pat. Off. |
| 0585751 | 3/1994 | European Pat. Off. |
| 0617014 | 9/1994 | European Pat. Off. |
| 94/01189 | 10/1995 | South Africa |
| 94/14761 | 7/1994 | WIPO |
| 94/19331 | 9/1994 | WIPO |

*Primary Examiner*—Johann Richter
*Assistant Examiner*—Ebenezer Sackey
*Attorney, Agent, or Firm*—Burns, Doane, Swecker & Mathis, L.L.P.

[57] ABSTRACT

Hydroximic acid derivatives, useful as pesticides, have the formula

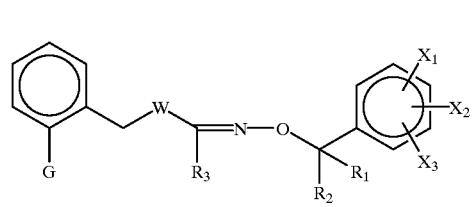

(I)

in which G is $G_3$ or $G_4$ having the formula:

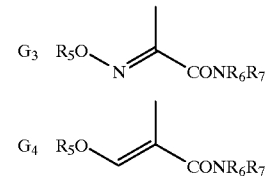

in which $R_5$ is lower alkyl; $R_6$ and $R_7$ are, independently, hydrogen or lower alkyl; W is O, S, SO or $SO_2$; $X_1$, $X_2$ and $X_3$ are, independently, hydrogen or a variety of substituents; and $R_1$, $R_2$ and $R_3$ are, independently, hydrogen or a variety of substituents.

44 Claims, No Drawings

HYDROXIMIC ACID DERIVATIVES

This application is a divisional of application Ser. No. 08/945,343, filed Feb. 10, 1998, now allowed, which is the U.S. national phase of International Application Ser. No. PCT/EP96/01386, filed Mar. 29, 1996 and designating the United States. Application Ser. No. 08/945,343 is incorporated by reference herein in its entirety and relied upon.

The present invention relates to new hydroximic acid derivatives for use in plant protection. It also relates to the fungicidal and arthropodicidal compositions based on these compounds and to the processes for controlling fungal diseases of crops, as well as destruction of arthropods, using these compounds.

Hydroximic acid derivatives for use in controlling fungal diseases are known from EP 463488 and from EP 370629.

One aim of the present invention is to provide a new family of hydroximic acid derivatives so as to have more choice in the available products. It is desirable indeed to have more products available so as to have various spectra of activity and to make it possible to have more appropriate control of fungal diseases according to the particular problems which are to be solved.

Another aim of the present invention is to provide new hydroximic acid derivatives which have improved properties in the treatment of fungal diseases and destructive arthropods of crops.

Another aim of the present invention is to provide compounds which have an improved use spectrum, in the field of fungal diseases, especially for the treatment of fungal diseases of rice, cereals, fruit trees and vegetables, vine grapes and sugar beet.

It has now been found that these aims could be achieved, in all or in part, by means of the products of the invention, described hereinbelow.

The invention provides compounds which are hydroximic acid derivatives of general formula (I):

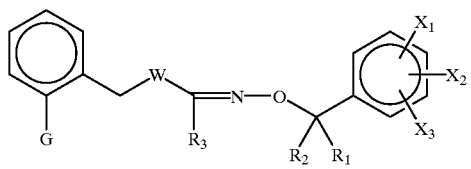

(I)

wherein:
G is either G1 or G2 or G3 or G4 of formula:

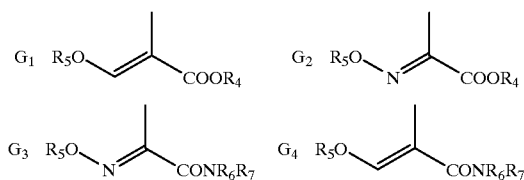

$X_1$, $X_2$, $X_3$ are independently a hydrogen or halogen atom; a hydroxy, mercapto, nitro, thiocyanato, azido group, cyano group;
a alkyl or haloalkyl group, cyanoalkyl, alkoxy, haloalkoxy, cyanoalkoxy, alkylthio, haloalkylthio, cyanoalkylthio, alkylsulfinyl, haloalkylsulfinyl, alkylsulfonyl, haloalkylsulfonyl, these alkyl or alkoxy being lower radicals,
a cycloalkyl or halocycloalkyl group, alkenyl, alkynyl, alkenyloxy, alkynyloxy, alkenylthio, alkynylthio, these alkyl or alkenyl or alkynyl being lower radicals,
an amino, alkylamino, dialkylamino, acylamino,
a lower alkoxycarbonyl group,
N-alkylcarbamoyl,
N,N-dialkylcarbamoyl,
N-alkylsulfamoyl,
N,N-dialkylsulfamoyl,
$R_1$, $R_2$ are independently a hydrogen atom, or a alkyl or haloalkyl, a cycloalkyl or halocycloalkyl, cyano, alkoxyalkyl, alkoxycarbonyl; or $R_1$ and $R_2$ can form together a divalent radical such as an alkylene group, these alkyl or alkoxy or alkylene being lower radicals,
$R_3$ is a hydrogen atom, or a alkyl or haloalkyl, a cycloalkyl or halocycloalkyl, alkenyl, alkynyl, alkoxyalkyl, alkylthioalkyl, cyanoalkyl, haloalkoxyalkyl, dialkylaminoalkyl, an optionnally substituted phenyl or an optionnally substituted benzyl group, these alkyl or alkoxy or alkenyl or alkynyl being lower radicals,
W is an oxygen or a sulfur atom. SO or $SO_2$
$R_4$–$R_5$ are a lower alkyl group,
$R_6$, $R_7$ are independently a hydrogen atom or a lower alkyl group.

In the compounds of formula (I), there are 4 different stereoisomers (E,E or E,Z or Z,E or Z,Z) depending on the configuration of each of the 2 double bonds. These E or Z denomination could be replaced by the corresponding name of syn and anti, or cis and trans. These denominations are well known in the art. In the instant specification, in such denomination EZ, EE or ZE or ZZ, the first letter refers to the configuration of the G group and the second letter refers to the configuration of the hydroximic group.

There may also be in some cases optically active carbons.

Formula (I) and the present invention include also the stereoisomers (including enantiomers) of these compounds, either separated or in mixtures.

In the present text, the generic terms have the following meanings:
halogen atom means a fluorine, chlorine, bromine or iodine atom;
the adjective "lower" qualifying an organic group means that this group has up to 6 carbons;
the alkyl groups may be linear or branched;
the denomination "hydroximic acid derivatives" includes both the actual "hydroximic acid derivatives" (with O—C=N—O group) and the "thiohydroximic acid derivatives" (with S—C=N—O).

More specific examples of groups which may be used in the invention are:
lower alkyl group such as methyl, ethyl, n-propyl, isopropyl, n-butyl, isobutyl, sec-butyl, tert-butyl, n-pentyl, neopentyl, tert-pentyl, hexyl group,
lower cycloalkyl group such as cyclopropyl, cyclobutyl, cyclopentyl, cyclohexyl group,
lower alkoxy group such as methoxy, ethoxy, propoxy, isopropoxy, butoxy, pentoxy group,
lower alkylthio group such as methylthio, ethylthio, propylthio, isopropylthio, butylthio, pentylthio,
lower haloalkyl group such as chloromethyl, bromomethyl, difluoromethyl, dichloromethyl, trifluoromethyl, 1-chloroethyl, 2-iodoethyl; 3-chloropropyl, 2-methyl-2-chloropropyl, lower haloalkoxy group such as trifluoromethoxy, difluoromethoxy, chlorodifluoromethoxy, 2-chloroethoxy, 1,1,2,2-tetrafluoroethoxy, 3-chloropropoxy, 2,2,2-trifluoroethoxy group alkoxycarbonyl group such as methoxycarbonyl, ethoxycarbonyl, isopropoxycarbonyl, lower dialkylamino group such as dimethylamino, ethylmethylamino, diethylamino, dipropylamino, diisopropylamino group; it also includes groups such as pyrrolidino, piperidino, morpholino.

Some embodiments of the compounds represented by the general formula (I) of the present invention are shown in Table 1 wherein $X_3=R_2=H$, $G=G_1$ or $G_2$ or $G_3$ or $G_4$. The definition of each abbreviation used in the table is the following: Me is methyl; Et is ethyl: n-Pr is n-propyl; i-Pr is isopropyl; cPr is cyclopropyl;

TABLE 1

| N° | G | R1, R2 | X1, X2 | R3 | W | R5 | R4 | R6, R7 |
|---|---|---|---|---|---|---|---|---|
| 1 | G1 | H; H | H, H | H | O | Me | Me | |
| 2 | G2 | H; H | H, H | H | O | Me | Me | |
| 3 | G3 | H; H | H, H | H | O | Me | | Me; H |
| 4 | G1 | H; H | H, H | Me | O | Me | Me | |
| 5 | G2 | H; H | H, H | Me | O | Me | Me | |
| 6 | G3 | H; H | H, H | Me | O | Me | | Me; H |
| 7 | G1 | H; H | H, H | Et | O | Me | Me | |
| 8 | G2 | H; H | H, H | Et | O | Me | Me | |
| 9 | G3 | H; H | H, H | Et | O | Me | | Me; H |
| 10 | G1 | H; H | H, H | iPr | O | Me | Me | |
| 11 | G2 | H; H | H, H | iPr | O | Me | Me | |
| 12 | G3 | H; H | H, H | iPr | O | Me | | Me; H |
| 13 | G1 | Me; H | H, H | H | O | Me | Me | |
| 14 | G2 | Me; H | H, H | H | O | Me | Me | |
| 15 | G3 | Me; H | H, H | H | O | Me | | Me; H |
| 16 | G1 | Me; H | H, H | Me | O | Me | Me | |
| 17 | G2 | Me; H | H, H | Me | O | Me | Me | |
| 18 | G3 | Me; H | H, H | Me | O | Me | | Me; H |
| 19 | G1 | Me; H | H, H | Et | O | Me | Me | |
| 20 | G2 | Me; H | H, H | Et | O | Me | Me | |
| 21 | G3 | Me; H | H, H | Et | O | Me | | Me; H |
| 22 | G1 | Me; H | H, H | iPr | O | Me | Me | |
| 23 | G2 | Me; H | H, H | iPr | O | Me | Me | |
| 24 | G3 | Me; H | H, H | iPr | O | Me | | Me; H |
| 25 | G1 | H; H | H, H | iPr | S | Me | Me | |
| 26 | G1 | H; H | 2-F | H | O | Me | Me | |
| 27 | G1 | H; H | 2-Cl | H | O | Me | Me | |
| 28 | G1 | H; H | 2-Me | H | O | Me | Me | |
| 29 | G1 | H; H | 2-CF$_3$ | H | O | Me | Me | |
| 30 | G1 | H; H | 2-CH$_3$O | H | O | Me | Me | |
| 31 | G1 | H; H | 2-CN | H | O | Me | Me | |
| 32 | G1 | H; H | 3-F | H | O | Me | Me | |
| 33 | G1 | H; H | 3-Cl | H | O | Me | Me | |
| 34 | G1 | H; H | 3-Me | H | O | Me | Me | |
| 35 | G1 | H; H | 3-CF$_3$ | H | O | Me | Me | |
| 36 | G1 | H; H | 3-CH$_3$O | H | O | Me | Me | |
| 37 | G1 | H; H | 3-CN | H | O | Me | Me | |
| 38 | G1 | H; H | 4-F | H | O | Me | Me | |
| 39 | G1 | H; H | 4-Cl | H | O | Me | Me | |
| 40 | G1 | H; H | 4-Me | H | O | Me | Me | |
| 41 | G1 | H; H | 4-CF$_3$ | H | O | Me | Me | |
| 42 | G1 | H; H | 4-CH$_3$O | H | O | Me | Me | |
| 43 | G1 | H; H | 4-CN | H | O | Me | Me | |
| 44 | G1 | H; H | 2,4-(F)$_2$ | H | O | Me | Me | |
| 45 | G2 | H; H | 2-F | H | O | Me | Me | |
| 46 | G2 | H; H | 2-Cl | H | O | Me | Me | |
| 47 | G2 | H; H | 2-Me | H | O | Me | Me | |
| 48 | G2 | H; H | 2-CF$_3$ | H | O | Me | Me | |
| 49 | G2 | H; H | 2-CH$_3$O | H | O | Me | Me | |
| 50 | G2 | H; H | 2-CN | H | O | Me | Me | |
| 51 | G2 | H; H | 3-F | H | O | Me | Me | |
| 52 | G2 | H; H | 3-Cl | H | O | Me | Me | |
| 53 | G2 | H; H | 3-Me | H | O | Me | Me | |
| 54 | G2 | H; H | 3-CF$_3$ | H | O | Me | Me | |
| 55 | G2 | H; H | 3-CH$_3$O | H | O | Me | Me | |
| 56 | G2 | H; H | 3-CN | H | O | Me | Me | |
| 57 | G2 | H; H | 4-F | H | O | Me | Me | |
| 58 | G2 | H; H | 4-Cl | H | O | Me | Me | |
| 59 | G2 | H; H | 4-Me | H | O | Me | Me | |
| 60 | G2 | H; H | 4-CF$_3$ | H | O | Me | Me | |
| 61 | G2 | H; H | 4-CH$_3$O | H | O | Me | Me | |
| 62 | G2 | H; H | 4-CN | H | O | Me | Me | |
| 63 | G2 | H; H | 2,4-(F)$_2$ | H | O | Me | Me | |
| 64 | G3 | H; H | 2-F | H | O | Me | | Me; H |
| 65 | G3 | H; H | 2-Cl | H | O | Me | | Me; H |
| 66 | G3 | H; H | 2-Me | H | O | Me | | Me; H |
| 67 | G3 | H; H | 2-CF$_3$ | H | O | Me | | Me; H |
| 68 | G3 | H; H | 2-CH$_3$O | H | O | Me | | Me; H |
| 69 | G3 | H; H | 2-CN | H | O | Me | | Me; H |
| 70 | G3 | H; H | 3-F | H | O | Me | | Me; H |
| 71 | G3 | H; H | 3-Cl | H | O | Me | | Me; H |
| 72 | G3 | H; H | 3-Me | H | O | Me | | Me; H |
| 73 | G3 | H; H | 3-CF$_3$ | H | O | Me | | Me; H |
| 74 | G3 | H; H | 3-CH$_3$O | H | O | Me | | Me; H |
| 75 | G3 | H; H | 3-CN | H | O | Me | | Me; H |
| 76 | G3 | H; H | 4-F | H | O | Me | | Me; H |
| 77 | G3 | H; H | 4-Cl | H | O | Me | | Me; H |
| 78 | G3 | H; H | 4-Me | H | O | Me | | Me; H |
| 79 | G3 | H; H | 4-CF$_3$ | H | O | Me | | Me; H |
| 80 | G3 | H; H | 4-CH$_3$O | H | O | Me | | Me; H |
| 81 | G3 | H; H | 4-CN | H | O | Me | | Me; H |
| 82 | G3 | H; H | 2,4-(F)$_2$ | H | O | Me | | Me; H |
| 83 | G1 | Me; H | 2-F | H | O | Me | Me | |
| 84 | G1 | Me; H | 2-Cl | H | O | Me | Me | |
| 85 | G1 | Me; H | 2-Me | H | O | Me | Me | |
| 86 | G1 | Me; H | 2-CF$_3$ | H | O | Me | Me | |
| 87 | G1 | Me; H | 2-CH$_3$O | H | O | Me | Me | |
| 88 | G1 | Me; H | 2-CN | H | O | Me | Me | |
| 89 | G1 | Me; H | 3-F | H | O | Me | Me | |
| 90 | G1 | Me; H | 3-Cl | H | O | Me | Me | |
| 91 | G1 | Me; H | 3-Me | H | O | Me | Me | |
| 92 | G1 | Me; H | 3-CF$_3$ | H | O | Me | Me | |
| 93 | G1 | Me; H | 3-CH$_3$O | H | O | Me | Me | |
| 94 | G1 | Me; H | 3-CN | H | O | Me | Me | |
| 95 | G1 | Me; H | 4-F | H | O | Me | Me | |
| 96 | G1 | Me; H | 4-Cl | H | O | Me | Me | |
| 97 | G1 | Me; H | 4-Me | H | O | Me | Me | |
| 98 | G1 | Me; H | 4-CF$_3$ | H | O | Me | Me | |
| 99 | G1 | Me; H | 4-CH$_3$O | H | O | Me | Me | |
| 100 | G1 | Me; H | 4-CN | H | O | Me | Me | |
| 101 | G1 | Me; H | 2,4-(F)$_2$ | H | O | Me | Me | |
| 102 | G2 | Me; H | 2-F | H | O | Me | Me | |
| 103 | G2 | Me; H | 2-Cl | H | O | Me | Me | |
| 104 | G2 | Me; H | 2-Me | H | O | Me | Me | |
| 105 | G2 | Me; H | 2-CF$_3$ | H | O | Me | Me | |
| 106 | G2 | Me; H | 2-CH$_3$O | H | O | Me | Me | |
| 107 | G2 | Me; H | 2-CN | H | O | Me | Me | |
| 108 | G2 | Me; H | 3-F | H | O | Me | Me | |
| 109 | G2 | Me; H | 3-Cl | H | O | Me | Me | |
| 110 | G2 | Me; H | 3-Me | H | O | Me | Me | |
| 111 | G2 | Me; H | 3-CF$_3$ | H | O | Me | Me | |
| 112 | G2 | Me; H | 3-CH$_3$O | H | O | Me | Me | |
| 113 | G2 | Me; H | 3-CN | H | O | Me | Me | |
| 114 | G2 | Me; H | 4-F | H | O | Me | Me | |
| 115 | G2 | Me; H | 4-Cl | H | O | Me | Me | |
| 116 | G2 | Me; H | 4-Me | H | O | Me | Me | |
| 117 | G2 | Me; H | 4-CF$_3$ | H | O | Me | Me | |
| 118 | G2 | Me; H | 4-CH$_3$O | H | O | Me | Me | |
| 119 | G2 | Me; H | 4-CN | H | O | Me | Me | |
| 120 | G2 | Me; H | 2,4-(F)$_2$ | H | O | Me | Me | |
| 121 | G3 | Me; H | 2-F | H | O | Me | | Me; H |
| 122 | G3 | Me; H | 2-Cl | H | O | Me | | Me; H |
| 123 | G3 | Me; H | 2-Me | H | O | Me | | Me; H |
| 124 | G3 | Me; H | 2-CF$_3$ | H | O | Me | | Me; H |
| 125 | G3 | Me; H | 2-CH$_3$O | H | O | Me | | Me; H |
| 126 | G3 | Me; H | 2-CN | H | O | Me | | Me; H |
| 127 | G3 | Me; H | 3-F | H | O | Me | | Me; H |
| 128 | G3 | Me; H | 3-Cl | H | O | Me | | Me; H |
| 129 | G3 | Me; H | 3-Me | H | O | Me | | Me; H |
| 130 | G3 | Me; H | 3-CF$_3$ | H | O | Me | | Me; H |
| 131 | G3 | Me; H | 3-CH$_3$O | H | O | Me | | Me; H |
| 132 | G3 | Me; H | 3-CN | H | O | Me | | Me; H |
| 133 | G3 | Me; H | 4-F | H | O | Me | | Me; H |

TABLE 1-continued

| N° | G | R1, R2 | X1, X2 | R3 | W | R5 | R4 | R6, R7 |
|---|---|---|---|---|---|---|---|---|
| 134 | G3 | Me; H | 4-Cl | H | O | Me | | Me; H |
| 135 | G3 | Me; H | 4-Me | H | O | Me | | Me; H |
| 136 | G3 | Me; H | 4-CF$_3$ | H | O | Me | | Me; H |
| 137 | G3 | Me; H | 4-CH$_3$O | H | O | Me | | Me; H |
| 138 | G3 | Me; H | 4-CN | H | O | Me | | Me; H |
| 139 | G3 | Me; H | 2,4-(F)$_2$ | H | O | Me | | Me; H |
| 140 | G1 | H; H | 2-F | Me | O | Me | Me | |
| 141 | G1 | H; H | 2-Cl | Me | O | Me | Me | |
| 142 | G1 | H; H | 2-Me | Me | O | Me | Me | |
| 143 | G1 | H; H | 2-CF$_3$ | Me | O | Me | Me | |
| 144 | G1 | H; H | 2-CH$_3$O | Me | O | Me | Me | |
| 145 | G1 | H; H | 2-CN | Me | O | Me | Me | |
| 146 | G1 | H; H | 3-F | Me | O | Me | Me | |
| 147 | G1 | H; H | 3-Cl | Me | O | Me | Me | |
| 148 | G1 | H; H | 3-Me | Me | O | Me | Me | |
| 149 | G1 | H; H | 3-CF$_3$ | Me | O | Me | Me | |
| 150 | G1 | H; H | 3-CH$_3$O | Me | O | Me | Me | |
| 151 | G1 | H; H | 3-CN | Me | O | Me | Me | |
| 152 | G1 | H; H | 4-F | Me | O | Me | Me | |
| 153 | G1 | H; H | 4-Cl | Me | O | Me | Me | |
| 154 | G1 | H; H | 4-Me | Me | O | Me | Me | |
| 155 | G1 | H; H | 4-CF$_3$ | Me | O | Me | Me | |
| 156 | G1 | H; H | 4-CH$_3$O | Me | O | Me | Me | |
| 157 | G1 | H; H | 4-CN | Me | O | Me | Me | |
| 158 | G1 | H; H | 2,4-(F)$_2$ | Me | O | Me | Me | |
| 159 | G2 | H; H | 2-F | Me | O | Me | Me | |
| 160 | G2 | H; H | 2-Cl | Me | O | Me | Me | |
| 161 | G2 | H; H | 2-Me | Me | O | Me | Me | |
| 162 | G2 | H; H | 2-CF$_3$ | Me | O | Me | Me | |
| 163 | G2 | H; H | 2-CH$_3$O | Me | O | Me | Me | |
| 164 | G2 | H; H | 2-CN | Me | O | Me | Me | |
| 165 | G2 | H; H | 3-F | Me | O | Me | Me | |
| 166 | G2 | H; H | 3-Cl | Me | O | Me | Me | |
| 167 | G2 | H; H | 3-Me | Me | O | Me | Me | |
| 168 | G2 | H; H | 3-CF$_3$ | Me | O | Me | Me | |
| 169 | G2 | H; H | 3-CH$_3$O | Me | O | Me | Me | |
| 170 | G2 | H; H | 3-CN | Me | O | Me | Me | |
| 171 | G2 | H; H | 4-F | Me | O | Me | Me | |
| 172 | G2 | H; H | 4-Cl | Me | O | Me | Me | |
| 173 | G2 | H; H | 4-Me | Me | O | Me | Me | |
| 174 | G2 | H; H | 4-CF$_3$ | Me | O | Me | Me | |
| 175 | G2 | H; H | 4-CH$_3$O | Me | O | Me | Me | |
| 176 | G2 | H; H | 4-CN | Me | O | Me | Me | |
| 177 | G2 | H; H | 2,4-(F)$_2$ | Me | O | Me | Me | |
| 178 | G3 | H; H | 2-F | Me | O | Me | | Me; H |
| 179 | G3 | H; H | 2-Cl | Me | O | Me | | Me; H |
| 180 | G3 | H; H | 2-Me | Me | O | Me | | Me; H |
| 181 | G3 | H; H | 2-CF$_3$ | Me | O | Me | | Me; H |
| 182 | G3 | H; H | 2-CH$_3$O | Me | O | Me | | Me; H |
| 183 | G3 | H; H | 2-CN | Me | O | Me | | Me; H |
| 184 | G3 | H; H | 3-F | Me | O | Me | | Me; H |
| 185 | G3 | H; H | 3-Cl | Me | O | Me | | Me; H |
| 186 | G3 | H; H | 3-Me | Me | O | Me | | Me; H |
| 187 | G3 | H; H | 3-CF$_3$ | Me | O | Me | | Me; H |
| 188 | G3 | H; H | 3-CH$_3$O | Me | O | Me | | Me; H |
| 189 | G3 | H; H | 3-CN | Me | O | Me | | Me; H |
| 190 | G3 | H; H | 4-F | Me | O | Me | | Me; H |
| 191 | G3 | H; H | 4-Cl | Me | O | Me | | Me; H |
| 192 | G3 | H; H | 4-Me | Me | O | Me | | Me; H |
| 193 | G3 | H; H | 4-CF$_3$ | Me | O | Me | | Me; H |
| 194 | G3 | H; H | 4-CH$_3$O | Me | O | Me | | Me; H |
| 195 | G3 | H; H | 4-CN | Me | O | Me | | Me; H |
| 196 | G3 | H; H | 2,4-(F)$_2$ | Me | O | Me | | Me; H |
| 197 | G1 | Me; H | 2-F | Me | O | Me | Me | |
| 198 | G1 | Me; H | 2-Cl | Me | O | Me | Me | |
| 199 | G1 | Me; H | 2-Me | Me | O | Me | Me | |
| 200 | G1 | Me; H | 2-CF$_3$ | Me | O | Me | Me | |
| 201 | G1 | Me; H | 2-CH$_3$O | Me | O | Me | Me | |
| 202 | G1 | Me; H | 2-CN | Me | O | Me | Me | |
| 203 | G1 | Me; H | 2-Br | Me | O | Me | Me | |
| 204 | G1 | Me; H | 2-MeS | Me | O | Me | Me | |
| 205 | G1 | Me; H | 2-CF$_3$O | Me | O | Me | Me | |
| 206 | G1 | Me; H | 2-CF$_3$ | Me | O | Me | Me | |
| 207 | G1 | Me; H | 2-NO$_2$ | Me | O | Me | Me | |
| 208 | G1 | Me; H | 2-Et | Me | O | Me | Me | |
| 209 | G1 | Me; H | 2-MeOC(O) | Me | O | Me | Me | |
| 210 | G1 | Me; H | 2-(Me)$_2$N | Me | O | Me | Me | |
| 211 | G1 | Me; H | 3-F | Me | O | Me | Me | |
| 212 | G1 | Me; H | 3-Cl | Me | O | Me | Me | |
| 213 | G1 | Me; H | 3-Me | Me | O | Me | Me | |
| 214 | G1 | Me; H | 3-CF$_3$ | Me | O | Me | Me | |
| 215 | G1 | Me; H | 3-CH$_3$O | Me | O | Me | Me | |
| 216 | G1 | Me; H | 3-CN | Me | O | Me | Me | |
| 217 | G1 | Me; H | 3-Br | Me | O | Me | Me | |
| 218 | G1 | Me; H | 3-MeS | Me | O | Me | Me | |
| 219 | G1 | Me; H | 3-CF$_3$O | Me | O | Me | Me | |
| 220 | G1 | Me; H | 3-CF$_3$S | Me | O | Me | Me | |
| 221 | G1 | Me; H | 3-NO$_2$ | Me | O | Me | Me | |
| 222 | G1 | Me; H | 3-Et | Me | O | Me | Me | |
| 223 | G1 | Me; H | 3-MeOC(O) | Me | O | Me | Me | |
| 224 | G1 | Me; H | 3-(Me)$_2$N | Me | O | Me | Me | |
| 225 | G1 | Me; H | 4-F | Me | O | Me | Me | |
| 226 | G1 | Me; H | 4-Cl | Me | O | Me | Me | |
| 227 | G1 | Me; H | 4-Me | Me | O | Me | Me | |
| 228 | G1 | Me; H | 4-CF$_3$ | Me | O | Me | Me | |
| 229 | G1 | Me; H | 4-CH$_3$O | Me | O | Me | Me | |
| 230 | G1 | Me; H | 4-CN | Me | O | Me | Me | |
| 231 | G1 | Me; H | 4-Br | Me | O | Me | Me | |
| 232 | G1 | Me; H | 4-MeS | Me | O | Me | Me | |
| 233 | G1 | Me; H | 4-CF$_3$O | Me | O | Me | Me | |
| 234 | G1 | Me; H | 4-CF$_3$ | Me | O | Me | Me | |
| 235 | G1 | Me; H | 4-NO$_2$ | Me | O | Me | Me | |
| 236 | G1 | Me; H | 4-Et | Me | O | Me | Me | |
| 237 | G1 | Me; H | 4-MeOC(O) | Me | O | Me | Me | |
| 238 | G1 | Me; H | 4-(Me)$_2$N | Me | O | Me | Me | |
| 239 | G1 | Me; H | 2,3-(F)$_2$ | Me | O | Me | Me | |
| 240 | G1 | Me; H | 2,4-(F)$_2$ | Me | O | Me | Me | |
| 241 | G1 | Me; H | 2,5-(F)$_2$ | Me | O | Me | Me | |
| 242 | G1 | Me; H | 2,6-(F)$_2$ | Me | O | Me | Me | |
| 243 | G1 | Me; H | 3,4-(F)$_2$ | Me | O | Me | Me | |
| 244 | G1 | Me; H | 3,5-(F)$_2$ | Me | O | Me | Me | |
| 245 | G1 | Me; H | 2,3-(Me)$_2$ | Me | O | Me | Me | |
| 246 | G1 | Me; H | 2,4-(Me)$_2$ | Me | O | Me | Me | |
| 247 | G1 | Me; H | 2,5-(Me)$_2$ | Me | O | Me | Me | |
| 248 | G1 | Me; H | 2,6-(Me)$_2$ | Me | O | Me | Me | |
| 249 | G1 | Me; H | 3,4-(Me)$_2$ | Me | O | Me | Me | |
| 250 | G1 | Me; H | 3,5-(Me)$_2$ | Me | O | Me | Me | |
| 251 | G1 | Me; H | 2,4-(F)$_2$ | Me | O | Me | Me | |
| 252 | G2 | Me; H | 2-F | Me | O | Me | Me | |
| 253 | G2 | Me; H | 2-Cl | Me | O | Me | Me | |
| 254 | G2 | Me; H | 2-Me | Me | O | Me | Me | |
| 255 | G2 | Me; H | 2-CF$_3$ | Me | O | Me | Me | |
| 256 | G2 | Me; H | 2-CH$_3$O | Me | O | Me | Me | |
| 257 | G2 | Me; H | 2-CN | Me | O | Me | Me | |
| 258 | G2 | Me; H | 3-F | Me | O | Me | Me | |
| 259 | G2 | Me; H | 3-Cl | Me | O | Me | Me | |
| 260 | G2 | Me; H | 3-Me | Me | O | Me | Me | |
| 261 | G2 | Me; H | 3-CF$_3$ | Me | O | Me | Me | |
| 262 | G2 | Me; H | 3-CH$_3$O | Me | O | Me | Me | |
| 263 | G2 | Me; H | 3-CN | Me | O | Me | Me | |
| 264 | G2 | Me; H | 4-F | Me | O | Me | Me | |
| 265 | G2 | Me; H | 4-Cl | Me | O | Me | Me | |
| 266 | G2 | Me; H | 4-Me | Me | O | Me | Me | |
| 267 | G2 | Me; H | 4-CF$_3$ | Me | O | Me | Me | |
| 268 | G2 | Me; H | 4-CH$_3$O | Me | O | Me | Me | |
| 269 | G2 | Me; H | 4-CN | Me | O | Me | Me | |
| 270 | G2 | Me; H | 2,4-(F)$_2$ | Me | O | Me | Me | |
| 271 | G3 | Me; H | 2-F | Me | O | Me | | Me; H |
| 272 | G3 | Me; H | 2-Cl | Me | O | Me | | Me; H |
| 273 | G3 | Me; H | 2-Me | Me | O | Me | | Me; H |
| 274 | G3 | Me; H | 2-CF$_3$ | Me | O | Me | | Me; H |
| 275 | G3 | Me; H | 2-CH$_3$O | Me | O | Me | | Me; H |
| 276 | G3 | Me; H | 2-CN | Me | O | Me | | Me; H |
| 277 | G3 | Me; H | 3-F | Me | O | Me | | Me; H |
| 278 | G3 | Me; H | 3-Cl | Me | O | Me | | Me; H |
| 279 | G3 | Me; H | 3-Me | Me | O | Me | | Me; H |
| 280 | G3 | Me; H | 3-CF$_3$ | Me | O | Me | | Me; H |
| 281 | G3 | Me; H | 3-CH$_3$O | Me | O | Me | | Me; H |
| 282 | G3 | Me; H | 3-CN | Me | O | Me | | Me; H |
| 283 | G3 | Me; H | 4-F | Me | O | Me | | Me; H |
| 284 | G3 | Me; H | 4-Cl | Me | O | Me | | Me; H |
| 285 | G3 | Me; H | 4-Me | Me | O | Me | | Me; H |
| 286 | G3 | Me; H | 4-CF$_3$ | Me | O | Me | | Me; H |
| 287 | G3 | Me; H | 4-CH$_3$O | Me | O | Me | | Me; H |

TABLE 1-continued

| N° | G | R1, R2 | X1, X2 | R3 | W | R5 | R4 | R6, R7 |
|---|---|---|---|---|---|---|---|---|
| 288 | G3 | Me; H | 4-CN | Me | O | Me |  | Me; H |
| 289 | G3 | Me; H | 2,4-(F)$_2$ | Me | O | Me |  | Me; H |
| 290 | G1 | Me; H | 2-F | Et | O | Me | Me |  |
| 291 | G1 | H; H | 2-Cl | Et | O | Me | Me |  |
| 292 | G1 | H; H | 2-Me | Et | O | Me | Me |  |
| 293 | G1 | H; H | 2-CF$_3$ | Et | O | Me | Me |  |
| 294 | G1 | H; H | 2-CH$_3$O | Et | O | Me | Me |  |
| 295 | G1 | H; H | 2-CN | Et | O | Me | Me |  |
| 296 | G1 | H; H | 3-F | Et | O | Me | Me |  |
| 297 | G1 | H; H | 3-Cl | Et | O | Me | Me |  |
| 298 | G1 | H; H | 3-Me | Et | O | Me | Me |  |
| 299 | G1 | H; H | 3-CF$_3$ | Et | O | Me | Me |  |
| 300 | G1 | H; H | 3-CH$_3$O | Et | O | Me | Me |  |
| 301 | G1 | H; H | 3-CN | Et | O | Me | Me |  |
| 302 | G1 | H; H | 4-F | Et | O | Me | Me |  |
| 303 | G1 | H; H | 4-Cl | Et | O | Me | Me |  |
| 304 | G1 | H; H | 4-Me | Et | O | Me | Me |  |
| 305 | G1 | H; H | 4-CF$_3$ | Et | O | Me | Me |  |
| 306 | G1 | H; H | 4-CH$_3$O | Et | O | Me | Me |  |
| 307 | G1 | H; H | 4-CN | Et | O | Me | Me |  |
| 308 | G1 | H; H | 2,4-(F)$_2$ | Et | O | Me | Me |  |
| 309 | G2 | H; H | 2-F | Et | O | Me | Me |  |
| 310 | G2 | H; H | 2-Cl | Et | O | Me | Me |  |
| 311 | G2 | H; H | 2-Me | Et | O | Me | Me |  |
| 312 | G2 | H; H | 2-CF$_3$ | Et | O | Me | Me |  |
| 313 | G2 | H; H | 2-CH$_3$O | Et | O | Me | Me |  |
| 314 | G2 | H; H | 2-CN | Et | O | Me | Me |  |
| 315 | G2 | H; H | 3-F | Et | O | Me | Me |  |
| 316 | G2 | H; H | 3-Cl | Et | O | Me | Me |  |
| 317 | G2 | H; H | 3-Me | Et | O | Me | Me |  |
| 318 | G2 | H; H | 3-CF$_3$ | Et | O | Me | Me |  |
| 319 | G2 | H; H | 3-CH$_3$O | Et | O | Me | Me |  |
| 320 | G2 | H; H | 3-CN | Et | O | Me | Me |  |
| 321 | G2 | H; H | 4-F | Et | O | Me | Me |  |
| 322 | G2 | H; H | 4-Cl | Et | O | Me | Me |  |
| 323 | G2 | H; H | 4-Me | Et | O | Me | Me |  |
| 324 | G2 | H; H | 4-CF$_3$ | Et | O | Me | Me |  |
| 325 | G2 | H; H | 4-CH$_3$O | Et | O | Me | Me |  |
| 326 | G2 | H; H | 4-CN | Et | O | Me | Me |  |
| 327 | G2 | H; H | 2,4-(F)$_2$ | Et | O | Me | Me |  |
| 328 | G3 | H; H | 2-F | Et | O | Me |  | Me; H |
| 329 | G3 | H; H | 2-Cl | Et | O | Me |  | Me; H |
| 330 | G3 | H; H | 2-Me | Et | O | Me |  | Me; H |
| 331 | G3 | H; H | 2-CF$_3$ | Et | O | Me |  | Me; H |
| 332 | G3 | H; H | 2-CH$_3$O | Et | O | Me |  | Me; H |
| 333 | G3 | H; H | 2-CN | Et | O | Me |  | Me; H |
| 334 | G3 | H; H | 3-F | Et | O | Me |  | Me; H |
| 335 | G3 | H; H | 3-Cl | Et | O | Me |  | Me; H |
| 336 | G3 | H; H | 3-Me | Et | O | Me |  | Me; H |
| 337 | G3 | H; H | 3-CF$_3$ | Et | O | Me |  | Me; H |
| 338 | G3 | H; H | 3-CH$_3$O | Et | O | Me |  | Me; H |
| 339 | G3 | H; H | 3-CN | Et | O | Me |  | Me; H |
| 340 | G3 | H; H | 4-F | Et | O | Me |  | Me; H |
| 341 | G3 | H; H | 4-Cl | Et | O | Me |  | Me; H |
| 342 | G3 | H; H | 4-Me | Et | O | Me |  | Me; H |
| 343 | G3 | H; H | 4-CF$_3$ | Et | O | Me |  | Me; H |
| 344 | G3 | H; H | 4-CH$_3$O | Et | O | Me |  | Me; H |
| 345 | G3 | H; H | 4-CN | Et | O | Me |  | Me; H |
| 346 | G3 | H; H | 2,4-(F)$_2$ | Et | O | Me |  | Me; H |
| 347 | G1 | Me; H | 2-F | Et | O | Me | Me |  |
| 348 | G1 | Me; H | 2-Cl | Et | O | Me | Me |  |
| 349 | G1 | Me; H | 2-Me | Et | O | Me | Me |  |
| 350 | G1 | Me; H | 2-CF$_3$ | Et | O | Me | Me |  |
| 351 | G1 | Me; H | 2-CH$_3$O | Et | O | Me | Me |  |
| 352 | G1 | Me; H | 2-CN | Et | O | Me | Me |  |
| 353 | G1 | Me; H | 3-F | Et | O | Me | Me |  |
| 354 | G1 | Me; H | 3-Cl | Et | O | Me | Me |  |
| 355 | G1 | Me; H | 3-Me | Et | O | Me | Me |  |
| 356 | G1 | Me; H | 3-CF$_3$ | Et | O | Me | Me |  |
| 357 | G1 | Me; H | 3-CH$_3$O | Et | O | Me | Me |  |
| 358 | G1 | Me; H | 3-CN | Et | O | Me | Me |  |
| 359 | G1 | Me; H | 4-F | Et | O | Me | Me |  |
| 360 | G1 | Me; H | 4-Cl | Et | O | Me | Me |  |
| 361 | G1 | Me; H | 4-Me | Et | O | Me | Me |  |
| 362 | G1 | Me; H | 4-CF$_3$ | Et | O | Me | Me |  |
| 363 | G1 | Me; H | 4-CH$_3$O | Et | O | Me | Me |  |
| 364 | G1 | Me; H | 4-CN | Et | O | Me | Me |  |
| 365 | G1 | Me; H | 2,4-(F)$_2$ | Et | O | Me | Me |  |
| 366 | G2 | Me; H | 2-F | Et | O | Me | Me |  |
| 367 | G2 | Me; H | 2-Cl | Et | O | Me | Me |  |
| 368 | G2 | Me; H | 2-Me | Et | O | Me | Me |  |
| 369 | G2 | Me; H | 2-CF$_3$ | Et | O | Me | Me |  |
| 370 | G2 | Me; H | 2-CH$_3$O | Et | O | Me | Me |  |
| 371 | G2 | Me; H | 2-CN | Et | O | Me | Me |  |
| 372 | G2 | Me; H | 3-F | Et | O | Me | Me |  |
| 373 | G2 | Me; H | 3-Cl | Et | O | Me | Me |  |
| 374 | G2 | Me; H | 3-Me | Et | O | Me | Me |  |
| 375 | G2 | Me; H | 3-CF$_3$ | Et | O | Me | Me |  |
| 376 | G2 | Me; H | 3-CH$_3$O | Et | O | Me | Me |  |
| 377 | G2 | Me; H | 3-CN | Et | O | Me | Me |  |
| 378 | G2 | Me; H | 4-F | Et | O | Me | Me |  |
| 379 | G2 | Me; H | 4-Cl | Et | O | Me | Me |  |
| 380 | G2 | Me; H | 4-Me | Et | O | Me | Me |  |
| 381 | G2 | Me; H | 4-CF$_3$ | Et | O | Me | Me |  |
| 382 | G2 | Me; H | 4-CH$_3$O | Et | O | Me | Me |  |
| 383 | G2 | Me; H | 4-CN | Et | O | Me | Me |  |
| 384 | G2 | Me; H | 2,4-(F)$_2$ | Et | O | Me | Me |  |
| 385 | G3 | Me; H | 2-F | Et | O | Me |  | Me; H |
| 386 | G3 | Me; H | 2-Cl | Et | O | Me |  | Me; H |
| 387 | G3 | Me; H | 2-Me | Et | O | Me |  | Me; H |
| 388 | G3 | Me; H | 2-CF$_3$ | Et | O | Me |  | Me; H |
| 389 | G3 | Me; H | 2-CH$_3$O | Et | O | Me |  | Me; H |
| 390 | G3 | Me; H | 2-CN | Et | O | Me |  | Me; H |
| 391 | G3 | Me; H | 3-F | Et | O | Me |  | Me; H |
| 392 | G3 | Me; H | 3-Cl | Et | O | Me |  | Me; H |
| 393 | G3 | Me; H | 3-Me | Et | O | Me |  | Me; H |
| 394 | G3 | Me; H | 3-CF$_3$ | Et | O | Me |  | Me; H |
| 395 | G3 | Me; H | 3-CH$_3$O | Et | O | Me |  | Me; H |
| 396 | G3 | Me; H | 3-CN | Et | O | Me |  | Me; H |
| 397 | G3 | Me; H | 4-F | Et | O | Me |  | Me; H |
| 398 | G3 | Me; H | 4-Cl | Et | O | Me |  | Me; H |
| 399 | G3 | Me; H | 4-Me | Et | O | Me |  | Me; H |
| 400 | G3 | Me; H | 4-CF$_3$ | Et | O | Me |  | Me; H |
| 401 | G3 | Me; H | 4-CH$_3$O | Et | O | Me |  | Me; H |
| 402 | G3 | Me; H | 4-CN | Et | O | Me |  | Me; H |
| 403 | G3 | Me; H | 2,4-(F)$_2$ | Et | O | Me |  | Me; H |
| 404 | G1 | Me; H | 2-F | iPr | O | Me | Me |  |
| 405 | G1 | Me; H | 2-Cl | iPr | O | Me | Me |  |
| 406 | G1 | H; H | 2-Me | iPr | O | Me | Me |  |
| 407 | G1 | H; H | 2-CF$_3$ | iPr | O | Me | Me |  |
| 408 | G1 | H; H | 2-CH$_3$O | iPr | O | Me | Me |  |
| 409 | G1 | H; H | 2-CN | iPr | O | Me | Me |  |
| 410 | G1 | H; H | 3-F | iPr | O | Me | Me |  |
| 411 | G1 | H; H | 3-Cl | iPr | O | Me | Me |  |
| 412 | G1 | H; H | 3-Me | iPr | O | Me | Me |  |
| 413 | G1 | H; H | 3-CF$_3$ | iPr | O | Me | Me |  |
| 414 | G1 | H; H | 3-CH$_3$O | iPr | O | Me | Me |  |
| 415 | G1 | H; H | 3-CN | iPr | O | Me | Me |  |
| 416 | G1 | H; H | 4-F | iPr | O | Me | Me |  |
| 417 | G1 | H; H | 4-Cl | iPr | O | Me | Me |  |
| 418 | G1 | H; H | 4-Me | iPr | O | Me | Me |  |
| 419 | G1 | H; H | 4-CF$_3$ | iPr | O | Me | Me |  |
| 420 | G1 | H; H | 4-CH$_3$O | iPr | O | Me | Me |  |
| 421 | G1 | H; H | 4-CN | iPr | O | Me | Me |  |
| 422 | G1 | H; H | 2,4-(F)$_2$ | iPr | O | Me | Me |  |
| 423 | G2 | H; H | 2-F | iPr | O | Me | Me |  |
| 424 | G2 | H; H | 2-Cl | iPr | O | Me | Me |  |
| 425 | G2 | H; H | 2-Me | iPr | O | Me | Me |  |
| 426 | G2 | H; H | 2-CF$_3$ | iPr | O | Me | Me |  |
| 427 | G2 | H; H | 2-CH$_3$O | iPr | O | Me | Me |  |
| 428 | G2 | H; H | 2-CN | iPr | O | Me | Me |  |
| 429 | G2 | H; H | 3-F | iPr | O | Me | Me |  |
| 430 | G2 | H; H | 3-Cl | iPr | O | Me | Me |  |
| 431 | G2 | H; H | 3-Me | iPr | O | Me | Me |  |
| 432 | G2 | H; H | 3-CF$_3$ | iPr | O | Me | Me |  |
| 433 | G2 | H; H | 3-CH$_3$O | iPr | O | Me | Me |  |
| 434 | G2 | H; H | 3-CN | iPr | O | Me | Me |  |
| 435 | G2 | H; H | 4-F | iPr | O | Me | Me |  |
| 436 | G2 | H; H | 4-Cl | iPr | O | Me | Me |  |
| 437 | G2 | H; H | 4-Me | iPr | O | Me | Me |  |
| 438 | G2 | H; H | 4-CF$_3$ | iPr | O | Me | Me |  |
| 439 | G2 | H; H | 4-CH$_3$O | iPr | O | Me | Me |  |
| 440 | G2 | H; H | 4-CN | iPr | O | Me | Me |  |
| 441 | G2 | H; H | 2,4-(F)$_2$ | iPr | O | Me | Me |  |

TABLE 1-continued

| N° | G | R1, R2 | X1, X2 | R3 | W | R5 | R4 | R6, R7 |
|---|---|---|---|---|---|---|---|---|
| 442 | G3 | H; H | 2-F | iPr | O | Me | | Me; H |
| 443 | G3 | H; H | 2-Cl | iPr | O | Me | | Me; H |
| 444 | G3 | H; H | 2-Me | iPr | O | Me | | Me; H |
| 445 | G3 | H; H | 2-CF$_3$ | iPr | O | Me | | Me; H |
| 446 | G3 | H; H | 2-CH$_3$O | iPr | O | Me | | Me; H |
| 447 | G3 | H; H | 2-CN | iPr | O | Me | | Me; H |
| 448 | G3 | H; H | 3-F | iPr | O | Me | | Me; H |
| 449 | G3 | H; H | 3-Cl | iPr | O | Me | | Me; H |
| 450 | G3 | H; H | 3-Me | iPr | O | Me | | Me; H |
| 451 | G3 | H; H | 3-CF$_3$ | iPr | O | Me | | Me; H |
| 452 | G3 | H; H | 3-CH$_3$O | iPr | O | Me | | Me; H |
| 453 | G3 | H; H | 3-CN | iPr | O | Me | | Me; H |
| 454 | G3 | H; H | 4-F | iPr | O | Me | | Me; H |
| 455 | G3 | H; H | 4-Cl | iPr | O | Me | | Me; H |
| 456 | G3 | H; H | 4-Me | iPr | O | Me | | Me; H |
| 457 | G3 | H; H | 4-CF$_3$ | iPr | O | Me | | Me; H |
| 458 | G3 | H; H | 4-CH$_3$O | iPr | O | Me | | Me; H |
| 459 | G3 | H; H | 4-CN | iPr | O | Me | | Me; H |
| 460 | G3 | H; H | 2,4-(F)$_2$ | iPr | O | Me | | Me; H |
| 461 | G1 | Me; H | 2-F | iPr | O | Me | Me | |
| 462 | G1 | Me; H | 2-Cl | iPr | O | Me | Me | |
| 463 | G1 | Me; H | 2-Me | iPr | O | Me | Me | |
| 464 | G1 | Me; H | 2-CF$_3$ | iPL | O | Me | Me | |
| 465 | G1 | Me; H | 2-CH$_3$O | iPr | O | Me | Me | |
| 466 | G1 | Me; H | 2-CN | iPr | O | Me | Me | |
| 467 | G1 | Me; H | 3-F | iPr | O | Me | Me | |
| 468 | G1 | Me; H | 3-Cl | iPr | O | Me | Me | |
| 469 | G1 | Me; H | 3-Me | iPr | O | Me | Me | |
| 470 | G1 | Me; H | 3-CF$_3$ | iPr | O | Me | Me | |
| 471 | G1 | Me; H | 3-CH$_3$O | iPr | O | Me | Me | |
| 472 | G1 | Me; H | 3-CN | iPr | O | Me | Me | |
| 473 | G1 | Me; H | 4-F | iPr | O | Me | Me | |
| 474 | G1 | Me; H | 4-Cl | iPr | O | Me | Me | |
| 475 | G1 | Me; H | 4-Me | iPr | O | Me | Me | |
| 476 | G1 | Me; H | 4-CF$_3$ | iPr | O | Me | Me | |
| 477 | G1 | Me; H | 4-CH$_3$O | iPr | O | Me | Me | |
| 478 | G1 | Me; H | 4-CN | iPr | O | Me | Me | |
| 479 | G1 | Me; H | 2,4-(F)$_2$ | iPr | O | Me | Me | |
| 480 | G2 | Me; H | 2-F | iPr | O | Me | Me | |
| 481 | G2 | Me; H | 2-Cl | iPr | O | Me | Me | |
| 482 | G2 | Me; H | 2-Me | iPr | O | Me | Me | |
| 483 | G2 | Me; H | 2-CF$_3$ | iPr | O | Me | Me | |
| 484 | G2 | Me; H | 2-CH$_3$O | iPr | O | Me | Me | |
| 485 | G2 | Me; H | 2-CN | iPr | O | Me | Me | |
| 486 | G2 | Me; H | 3-F | iPr | O | Me | Me | |
| 487 | G2 | Me; H | 3-Cl | iPr | O | Me | Me | |
| 488 | G2 | Me; H | 3-Me | iPr | O | Me | Me | |
| 489 | G2 | Me; H | 3-CF$_3$ | iPr | O | Me | Me | |
| 490 | G2 | Me; H | 3-CH$_3$O | iPr | O | Me | Me | |
| 491 | G2 | Me; H | 3-CN | iPr | O | Me | Me | |
| 492 | G2 | Me; H | 4-F | iPr | O | Me | Me | |
| 493 | G2 | Me; H | 4-Cl | iPr | O | Me | Me | |
| 494 | G2 | Me; H | 4-Me | iPr | O | Me | Me | |
| 495 | G2 | Me; H | 4-CF$_3$ | iPr | O | Me | Me | |
| 496 | G2 | Me; H | 4-CH$_3$O | iPr | O | Me | Me | |
| 497 | G2 | Me; H | 4-CN | iPr | O | Me | Me | |
| 498 | G2 | Me; H | 2,4-(F)$_2$ | iPr | O | Me | Me | |
| 499 | G3 | Me; H | 2-F | iPr | O | Me | | Me; H |
| 500 | G3 | Me; H | 2-Cl | iPr | O | Me | | Me; H |
| 501 | G3 | Me; H | 2-Me | iPr | O | Me | | Me; H |
| 502 | G3 | Me; H | 2-CF$_3$ | iPr | O | Me | | Me; H |
| 503 | G3 | Me; H | 2-CH$_3$O | iPr | O | Me | | Me; H |
| 504 | G3 | Me; H | 2-CN | iPr | O | Me | | Me; H |
| 505 | G3 | Me; H | 3-F | iPr | O | Me | | Me; H |
| 506 | G3 | Me; H | 3-Cl | iPr | O | Me | | Me; H |
| 507 | G3 | Me; H | 3-Me | iPr | O | Me | | Me; H |
| 508 | G3 | Me; H | 3-CF$_3$ | iPr | O | Me | | Me; H |
| 509 | G3 | Me; H | 3-CH$_3$O | iPr | O | Me | | Me; H |
| 510 | G3 | Me; H | 3-CN | iPr | O | Me | | Me; H |
| 511 | G3 | Me; H | 4-F | iPr | O | Me | | Me; H |
| 512 | G3 | Me; H | 4-Cl | iPr | O | Me | | Me; H |
| 513 | G3 | Me; H | 4-Me | iPr | O | Me | | Me; H |
| 514 | G3 | Me; H | 4-CF$_3$ | iPr | O | Me | | Me; H |
| 515 | G3 | Me; H | 4-CH$_3$O | iPr | O | Me | | Me; H |
| 516 | G3 | Me; H | 4-CN | iPr | O | Me | | Me; H |
| 517 | G3 | Me; H | 2,4-(F)$_2$ | iPr | O | Me | | Me; H |
| 518 | G1 | H; H | 2-F | cPr | O | Me | Me | |
| 519 | G1 | H; H | 2-Cl | cPr | O | Me | Me | |
| 520 | G1 | H; H | 2-Me | cPr | O | Me | Me | |
| 521 | G1 | H; H | 2-CF$_3$ | cPr | O | Me | Me | |
| 522 | G1 | H; H | 2-CH$_3$O | cPr | O | Me | Me | |
| 523 | G1 | H; H | 2-CN | cPr | O | Me | Me | |
| 524 | G1 | H; H | 3-F | cPr | O | Me | Me | |
| 525 | G1 | H; H | 3-Cl | cPr | O | Me | Me | |
| 526 | G1 | H; H | 3-Me | cPr | O | Me | Me | |
| 527 | G1 | H; H | 3-CF$_3$ | cPr | O | Me | Me | |
| 528 | G1 | H; H | 3-CH$_3$O | cPr | O | Me | Me | |
| 529 | G1 | H; H | 3-CN | cPr | O | Me | Me | |
| 530 | G1 | H; H | 4-F | cPr | O | Me | Me | |
| 531 | G1 | H; H | 4-Cl | cPr | O | Me | Me | |
| 532 | G1 | H; H | 4-Me | cPr | O | Me | Me | |
| 533 | G1 | H; H | 4-CF$_3$ | cPr | O | Me | Me | |
| 534 | G1 | H; H | 4-CH$_3$O | cPr | O | Me | Me | |
| 535 | G1 | H; H | 4-CN | cPr | O | Me | Me | |
| 536 | G1 | H; H | 2,4-(F)$_2$ | cPr | O | Me | Me | |
| 537 | G2 | H; H | 2-F | cPr | O | Me | Me | |
| 538 | G2 | H; H | 2-Cl | cPr | O | Me | Me | |
| 539 | G2 | H; H | 2-Me | cPr | O | Me | Me | |
| 540 | G2 | H; H | 2-CF$_3$ | cPr | O | Me | Me | |
| 541 | G2 | H; H | 2-CH$_3$O | cPr | O | Me | Me | |
| 542 | G2 | H; H | 2-CN | cPr | O | Me | Me | |
| 543 | G2 | H; H | 3-F | cPr | O | Me | Me | |
| 544 | G2 | H; H | 3-Cl | cPr | O | Me | Me | |
| 545 | G2 | H; H | 3-Me | cPr | O | Me | Me | |
| 546 | G2 | H; H | 3-CF$_3$ | cPr | O | Me | Me | |
| 547 | G2 | H; H | 3-CH$_3$O | cPr | O | Me | Me | |
| 548 | G2 | H; H | 3-CN | cPr | O | Me | Me | |
| 549 | G2 | H; H | 4-F | cPr | O | Me | Me | |
| 550 | G2 | H; H | 4-Cl | cPr | O | Me | Me | |
| 551 | G2 | H; H | 4-Me | cPr | O | Me | Me | |
| 552 | G2 | H; H | 4-CF$_3$ | cPr | O | Me | Me | |
| 553 | G2 | H; H | 4-CH$_3$O | cPr | O | Me | Me | |
| 554 | G2 | H; H | 4-CN | cPr | O | Me | Me | |
| 555 | G2 | H; H | 2,4-(F)$_2$ | cPr | O | Me | Me | |
| 556 | G3 | H; H | 2-F | cPr | O | Me | | Me; H |
| 557 | G3 | H; H | 2-Cl | cPr | O | Me | | Me; H |
| 558 | G3 | H; H | 2-Me | cPr | O | Me | | Me; H |
| 559 | G3 | H; H | 2-CF$_3$ | cPr | O | Me | | Me; H |
| 560 | G3 | H; H | 2-CH$_3$O | cPr | O | Me | | Me; H |
| 561 | G3 | H; H | 2-CN | cPr | O | Me | | Me; H |
| 562 | G3 | H; H | 3-F | cPr | O | Me | | Me; H |
| 563 | G3 | H; H | 3-Cl | cPr | O | Me | | Me; H |
| 564 | G3 | H; H | 3-Me | cPr | O | Me | | Me; H |
| 565 | G3 | H; H | 3-CF$_3$ | cPr | O | Me | | Me; H |
| 566 | G3 | H; H | 3-CH$_3$O | cPr | O | Me | | Me; H |
| 567 | G3 | H; H | 3-CN | cPr | O | Me | | Me; H |
| 568 | G3 | H; H | 4-F | cPr | O | Me | | Me; H |
| 569 | G3 | H; H | 4-Cl | cPr | O | Me | | Me; H |
| 570 | G3 | H; H | 4-Me | cPr | O | Me | | Me; H |
| 571 | G3 | H; H | 4-CF$_3$ | cPr | O | Me | | Me; H |
| 572 | G3 | H; H | 4-CH$_3$O | cPr | O | Me | | Me; H |
| 573 | G3 | H; H | 4-CN | cPr | O | Me | | Me; H |
| 574 | G3 | H; H | 2,4-(F)$_2$ | cPr | O | Me | | Me; H |
| 575 | G1 | Me; H | 2-F | cPr | O | Me | Me | |
| 576 | G1 | Me; H | 2-Cl | cPr | O | Me | Me | |
| 577 | G1 | Me; H | 2-Me | cPr | O | Me | Me | |
| 578 | G1 | Me; H | 2-CF$_3$ | cPr | O | Me | Me | |
| 579 | G1 | Me; H | 2-CH$_3$O | cPr | O | Me | Me | |
| 580 | G1 | Me; H | 2-CN | cPr | O | Me | Me | |
| 581 | G1 | Me; H | 3-F | cPr | O | Me | Me | |
| 582 | G1 | Me; H | 3-Cl | cPr | O | Me | Me | |
| 583 | G1 | Me; H | 3-Me | cPr | O | Me | Me | |
| 584 | G1 | Me; H | 3-CF$_3$ | cPr | O | Me | Me | |
| 585 | G1 | Me; H | 3-CH$_3$O | cPr | O | Me | Me | |
| 586 | G1 | Me; H | 3-CN | cPr | O | Me | Me | |
| 587 | G1 | Me; H | 4-F | cPr | Q | Me | Me | |
| 588 | G1 | Me; H | 4-Cl | cPr | O | Me | Me | |
| 589 | G1 | Me; H | 4-Me | cPr | O | Me | Me | |
| 590 | G1 | Me; H | 4-CF$_3$ | cPr | O | Me | Me | |
| 591 | G1 | Me; H | 4-CH$_3$O | cPr | O | Me | Me | |
| 592 | G1 | Me; H | 4-CN | cPr | O | Me | Me | |
| 593 | G1 | Me; H | 2,4-(F)$_2$ | cPr | O | Me | Me | |
| 594 | G2 | Me; H | 2-F | cPr | O | Me | Me | |
| 595 | G2 | Me; H | 2-Cl | cPr | O | Me | Me | |

TABLE 1-continued

| N° | G | R1, R2 | X1, X2 | R3 | W | R5 | R4 | R6, R7 |
|---|---|---|---|---|---|---|---|---|
| 596 | G2 | Me; H | 2-Me | cPr | O | Me | Me | |
| 597 | G2 | Me; H | 2-CF$_3$ | cPr | O | Me | Me | |
| 598 | G2 | Me; H | 2-CH$_3$O | cPr | O | Me | Me | |
| 599 | G2 | Me; H | 2-CN | cPr | O | Me | Me | |
| 600 | G2 | Me; H | 3-F | cPr | O | Me | Me | |
| 601 | G2 | Me; H | 3-Cl | cPr | O | Me | Me | |
| 602 | G2 | Me; H | 3-Me | cPr | O | Me | Me | |
| 603 | G2 | Me; H | 3-CF$_3$ | cPr | O | Me | Me | |
| 604 | G2 | Me; H | 3-CH$_3$O | cPr | O | Me | Me | |
| 605 | G2 | Me; H | 3-CN | cPr | O | Me | Me | |
| 606 | G2 | Me; H | 4-F | cPr | O | Me | Me | |
| 607 | G2 | Me; H | 4-Cl | cPr | O | Me | Me | |
| 608 | G2 | Me; H | 4-Me | cPr | O | Me | Me | |
| 609 | G2 | Me; H | 4-CF$_3$ | cPr | O | Me | Me | |
| 610 | G2 | Me; H | 4-CH$_3$O | cPr | O | Me | Me | |
| 611 | G2 | Me; H | 4-CN | cPr | O | Me | Me | |
| 612 | G2 | Me; H | 2,4-(F)$_2$ | cPr | O | Me | Me | |
| 613 | G3 | Me; H | 2-F | cPr | O | Me | | Me; H |
| 614 | G3 | Me; H | 2-Cl | cPr | O | Me | | Me; H |
| 615 | G3 | Me; H | 2-Me | cPr | O | Me | | Me; H |
| 616 | G3 | Me; H | 2-CF$_3$ | cPr | O | Me | | Me; H |
| 617 | G3 | Me; H | 2-CH$_3$O | cPr | O | Me | | Me; H |
| 618 | G3 | Me; H | 2-CN | cPr | O | Me | | Me; H |
| 619 | G3 | Me; H | 3-F | cPr | O | Me | | Me; H |
| 620 | G3 | Me; H | 3-Cl | cPr | O | Me | | Me; H |
| 621 | G3 | Me; H | 3-Me | cPr | O | Me | | Me; H |
| 622 | G3 | Me; H | 3-CF$_3$ | cPr | O | Me | | Me; H |
| 623 | G3 | Me; H | 3-CH$_3$O | cPr | O | Me | | Me; H |
| 624 | G3 | Me; H | 3-CN | cPr | O | Me | | Me; H |
| 625 | G3 | Me; H | 4-F | cPr | O | Me | | Me; H |
| 626 | G3 | Me; H | 4-Cl | cPr | O | Me | | Me; H |
| 627 | G3 | Me; H | 4-Me | cPr | O | Me | | Me; H |
| 628 | G3 | Me; H | 4-CF$_3$ | cPr | O | Me | | Me; H |
| 629 | G3 | Me; H | 4-CH$_3$O | cPr | O | Me | | Me; H |
| 630 | G3 | Me; H | 4-CN | cPr | O | Me | | Me; H |
| 631 | G3 | Me; H | 2,4-(F)$_2$ | cPr | O | Me | | Me; H |
| 632 | G1 | H; H | H, H | H | S | Me | Me | |
| 633 | G1 | H; H | H, H | Me | S | Me | Me | |
| 634 | G1 | H; H | H, H | Et | S | Me | Me | |
| 635 | G2 | H; H | H, H | H | S | Me | Me | |
| 636 | G2 | H; H | H, H | Me | S | Me | Me | |
| 637 | G2 | H; H | H, H | Et | S | Me | Me | |
| 638 | G3 | H; H | H, H | H | S | Me | | Me; H |
| 639 | G3 | H; H | H, H | Me | S | Me | | Me; H |
| 640 | G3 | H; H | H, H | Et | S | Me | | Me; H |
| 641 | G1 | H; H | H, H | H | SO | Me | Me | |
| 642 | G1 | H; H | H, H | Me | SO | Me | Me | |
| 643 | G1 | H; H | H, H | Et | SO | Me | Me | |
| 644 | G2 | H; H | H, H | H | SO | Me | Me | |
| 645 | G2 | H; H | H, H | Me | SO | Me | Me | |
| 646 | G2 | H; H | H, H | Et | SO | Me | Me | |
| 647 | G3 | H; H | H, H | H | SO | Me | | Me; H |
| 648 | G3 | H; H | H, H | Me | SO | Me | | Me; H |
| 649 | G3 | H; H | H, H | Et | SO | Me | | Me; H |
| 650 | G1 | H; H | H, H | H | SO$_2$ | Me | Me | |
| 651 | G1 | H; H | H, H | Me | SO$_2$ | Me | Me | |
| 652 | G1 | H; H | H, H | Et | SO$_2$ | Me | Me | |
| 653 | G2 | H; H | H, H | H | SO$_2$ | Me | Me | |
| 654 | G2 | H; H | H, H | Me | SO$_2$ | Me | Me | |
| 655 | G2 | H; H | H, H | Et | SO$_2$ | Me | Me | |
| 656 | G3 | H; H | H, H | H | SO$_2$ | Me | | Me; H |
| 657 | G3 | H; H | H, H | Me | SO$_2$ | Me | | Me; H |
| 658 | G3 | H; H | H, H | Et | SO$_2$ | Me | | Me; H |
| 659 | G1 | H; H | H, H | cPr | O | Me | Me | |
| 660 | G2 | H; H | H, H | cPr | O | Me | Me | |
| 661 | G3 | H; H | H, H | cPr | O | Me | | Me; H |
| 662 | G1 | Me; H | H, H | cPr | O | Me | Me | |
| 663 | G2 | Me; H | H, H | cPr | O | Me | Me | |
| 664 | G3 | Me; H | H, H | cPr | O | Me | | Me; H |

The preferred compounds of formula (I), for fungicidal uses as well as for arthropodicidal uses, are those in which:

when G is G$_1$ or G$_2$, R$_4$ is methyl: R$_5$ is methyl; or when G is G$_3$ or G$_4$, R$_5$ is methyl: R$_6$ is methyl and R$_7$ is hydrogen.

A still more preferred class of pesticides are those in which R$_3$ is a hydrogen atom, a lower alkyl or cycloalkyl group.

A still more preferred class of pesticides are those in which R$_1$ is a hydrogen atom or a lower alkyl or cycloalkyl, cyano, alkoxycarbonyl, haloalkylgroup and R$_2$ is hydrogen or methyl.

A still more preferred class of pesticides are those in which X$_3$ is H and X$_1$ or X$_2$ are alkyl, cyano, halogen, haloalkyl, alkoxy, haloalkoxy.

A still more preferred class of pesticides are those in which both double bonds in the formula (I) as shown hereinbefore are of E configuration.

A particularly preferred class of fungicides are compounds of formula (I) in which X1 is methyl or hydrogen, X2 and X3 are hydrogen; R$_1$ is hydrogen or methyl; R$_2$ is hydrogen; R$_3$ is hydrogen or lower alkyl group; W is an oxygen atom.

The compounds of the present invention characterized by the general formula (I) above can be prepared by at least one of the following methods A or B or C or D. The manufacturing process of the reactants used in these methods are generally known per se, and are generally described in the prior art either specifically, or in such a way that the man skilled in the art may adapt for the present purpose. The prior art which may be used by the man skilled in the art to determine the proper details of the manufacturing methods, may be found in general handbooks of chemistry as well as in the "Chemical Abstracts" and the computerized data bases which are open or available to the public.

Method A

A compound of formula (I) can be prepared by reacting a compound (hydroxamate derivative) of formula (II) and a compound of formula (III) in the presence of an acid binding agent (i.e. a basic, organic or inorganic, agent), optionally in the presence of a solvent, according to scheme (1):

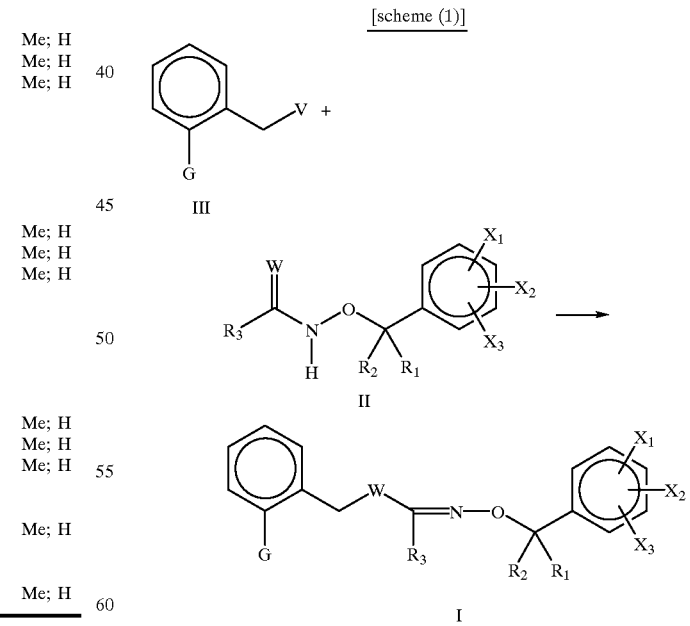

wherein, R$_1$, R$_2$, R$_3$, W, X$_1$, X$_2$, X$_3$, G, are the same as defined in the general formula (I) above; V is a halogen atom.

Reaction temperature is generally from −80° C. to 150° C. or to the boiling point of solvent used. As a solvent for this reaction, any inert solvent may be used with the starting materials, for example aliphatic hydrocarbons such as pentane, hexane, heptane, octane; aromatic hydrocarbons such as benzene, toluene, xylene, halobenzene; ethers such as diethylether, diisopropylether, tetrahydrofuran, dioxane, dimethoxyethane; halogenated hydrocarbons such as dichloromethane, chloroform and dichloroethane; esters such as methylacetate, ethylacetate; nitriles such as acetonitrile, propionitrile; dimethylformamide, dimethylsulfoxide, water. Mixtures of solvents may also be used as deemed appropriate by the man skilled in the art. The reaction time depending on the reaction conditions, is usually in the range of 0.1 to 24 hours.

As acid binding agents (also called basic agents), there can be cited, for example, the alkaline or alkaline-earth metallic hydroxides, hydrides, carbonates or bicarbonates, such as sodium hydroxide, potassium hydroxide, cesium hydroxide, calcium hydroxide; sodium carbonate, potassium carbonate, cesium carbonate, calcium carbonate, sodium bicarbonate, potassium bicarbonate, cesium bicarbonate; sodium hydride, potassium hydride, cesium hydride; and organic bases, especially nitrogen containing bases such as the pyridine derivatives for example pyridine or N,N-dimethylpyridine; the alkylamines, for example triethylamine; the diaza derivatives, for example diazabicycloundecene, diazabicyclooctane.

There is no strict limitation for the ratio of the compound of formula (III) versus the compound of formula (II). However it is generally convenient to use a molar ratio of compound of formula (III) to the compound of formula (II) within the range from 0.5 to 2, preferably 0.9 to 1.1.

The resulting compound of formula (I) may be isolated (as far as desired or deemed useful) and purified by already known methods per se, for example, extraction, recrystallization, chromatography.

The starting materials in the reaction of scheme (1) are hydroxamic or thiohydroxamic acid derivatives of formula (II). They can be prepared, for example, by the following reaction schemes (2) or (3), although there is no special limit for the preparation.

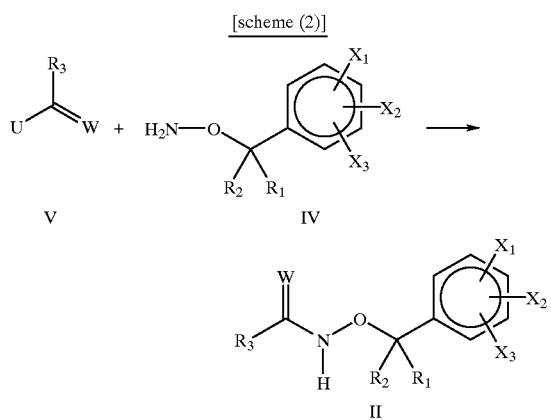

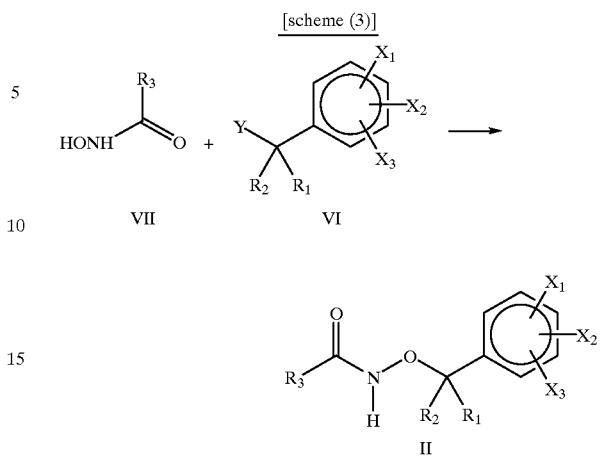

wherein, $R_1$, $R_2$, R3, W, X1, X2, X3, G are the same as defined in the general formula (I) above; Y is a halogen atom, alkylsulfonyloxy group or arylsulfonyloxy group; U is a halogen atom, or a hydroxy, alkoxy, amino, or a O—C (=O)R'3 group, R'3 has the same definition as R3 and is similar or different from R3, preferably a halogen atom whereby the compound of formula (V) is an acid halide.

According to reaction scheme (2), a hydroxamic or thiohydroxamic acid derivative of formula (II) can be prepared by reacting a hydroxylamine derivative of general formula (IV) with a compound, e.g. carboxylic acid or acid halide or anhydride, of general formula (V), in the presence of an acid binding material or a dehydrating agent, optionally in the further presence of a solvent for the reactants.

The general reaction conditions which may be used for the reaction of scheme (2) are similar or identical to the reaction conditions as described for the reaction of scheme (1), except that a dehydrating agent may also be used instead of the acid binding agent. As dehydrating or dehydration agents, carboxylic acid anhydrides may also be used, for example acetic anhydride or propionic anhydride. Directions to run a process according to scheme (2) are known and may be found in HOUBEN-WEYL, Methoden der organischen Chemie, Band E5, pages 1144–1149.

According to reaction scheme (3), a hydroxamic acid derivative of formula (II) can be prepared by reacting a benzyl derivative of general formula (VI) with a hydroxamic derivative of general formula (VII), optionally in the further presence of a solvent for the reactants.

The general reaction conditions which may be used for the reaction of scheme (3) are similar or identical to the reaction conditions as described for reaction of scheme (1). Directions to run a process according to scheme (3) are known and may be found in HOUBEN-WEYL, Methoden der organischen Chemie, Band E5, pages 1148–1149.

Halogenated benzyl derivatives of formula (III) where the stereochemistry of the G group is Z or E, starting material in the reaction scheme 1 above, can be prepared by already known methods per se, or by related preparation methods thereto. Such compounds and corresponding detailed manufacturing process are known in the art, for example in European patent applications 426460, 398692, 617014, 585751, 487409, 535928 or german patent application 4305502. Other benzyl derivatives of formula (III) can also be prepared by the application or adaptation of methods known per se.

Thiohydroxamic acid derivatives of formula (II), wherein, $R_1$, $R_2$, $R_3$, X1, X2, X3, are the same as defined in the general formula (I) above and W is sulfur, are also a feature of the present invention. They can be prepared by thionation of an hydroxamic acid by using a thionation reagent such as phosphorus pentasulfide or "Lawesson reagent" according to a method such as decribed (or similar to it) in HOUBEN-WEYL, Methoden der organischen Chemie, Band E5, pages 1279–1280 and in Synthesis, 1984, 829–831.

SCHEME 4:

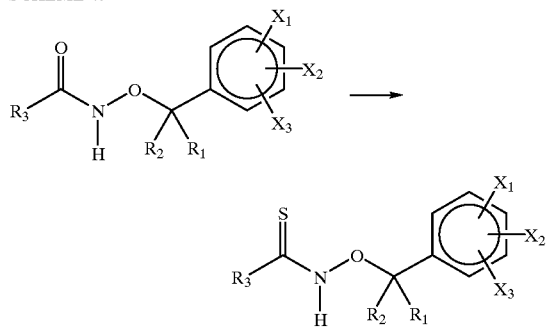

Method B

A compound represented by the general formula (I) where G is G3 or G4 can be prepared by reacting a compound of formula I-1 (which is a formula I wherein G is G1 or G2) with methylamine according to the following reaction scheme:

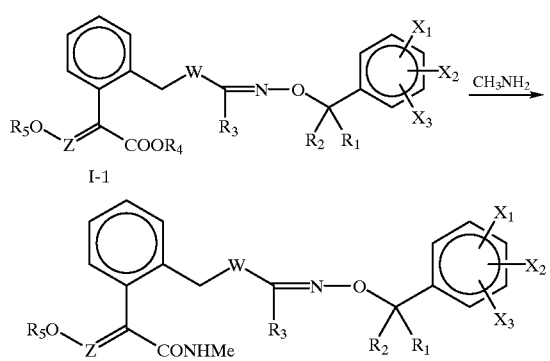

wherein, $R_1$, $R_2$, R3, R4, R5, W, X1, X2, X3, are the same as defined previously in the general formula (I) and Z is N or CH.

Reaction temperatures are generally from −50° C. to 100° C. or the boiling point of solvent used. The reaction is preferably performed in alcoholic solvents such as methanol or ethanol or isopropanol There is no strict limitation for the ratio of the compound of formula (I-1) versus the methylamine. However it is generally convenient to use a molar ratio of methylamine to the compound of formula (I-1) within the range from 1 to 5, preferably 1.1 to 2.

Method C

A compound represented by the general formula (I) as prepared by means of method A has generally and mainly a Z stereochemistry on the hydroximic moiety of the molecule. E isomers may be prepared from Z isomers by heating in a solvent preferably under UV irradiation and/or in the presence of an acid catalyst. The reaction is run up to the time that the proper and desired transformation rate of a Z isomer into an E is obtained. The reaction temperature is generally in the range from 0° to the boiling point of the solvent. As a solvent for this reaction, any inert solvent may be used with the starting materials, for example aliphatic hydrocarbons such as pentane, hexane, heptane, octane; aromatic hydrocarbons such as benzene, toluene, xylene, chlorobenzene; ethers such as diethyl ether, diisopropyl ether, tetrahydrofuran, dioxane, dimethoxyethane; halogenated hydrocarbons such as dichloromethane, chloroform and dichloroethane; alcohols such as methanol, ethanol, isopropanol; esters such as methylacetate, ethylacetate; nitriles such as acetonitrile, propionitrile; dimethylformamide, dimethylsulfoxide, water. Mixtures of solvents may also be used as deemed appropriate by the man skilled in the art.

The solvent is preferably an aromatic solvent, e.g. toluene or xylene or an ether such as diisopropylether.

The acid is preferably an anhydrous hydracid such as HCl or a carboxylic acid such as acetic or propionic acid or a sulfonic acid such as methanesulfonic acid, paratoluenesulfonic acid or sulfuric acid.

Method D

The compounds of formula I wherein W is SO or SO2 (and $R_1$, $R_2$, $R_3$, $X_1$, $X_2$, $X_3$, G may be the same as defined herein above) can be prepared from compounds of general formula I wherein W is sulfur by oxidation by mean of an oxidising agent in an inert solvent. By oxidizing agent one can use, organic or mineral peroxides such as metachloroperbenzoic acid, hydroperoxides, mineral oxychloride or oxygen in presence of a catalyst. The following scheme describes such reactions.

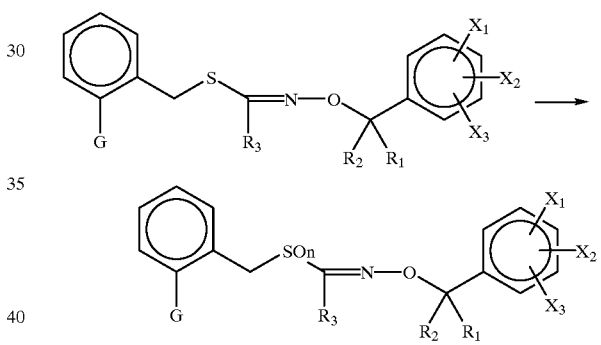

As usual the substituents in these scheme have the same general meaning as in the previous general formula The invention provides a method for combatting fungal diseases of plants at a locus which comprises applying thereto an effective amount of a compound of formula (I).

The invention also relates to a process for the treatment of cultivated plants affected or capable of being affected by fungal diseases, characterized in that an effective dose of a compound according to the formula (I) is applied to the plants. Effective dose is understood to mean an amount sufficient to make possible control or destruction of the fungi present on these cultivated plants. The use doses can, however, vary within wide limits depending on, for example, the fungus to be controlled, type of crop, the weather conditions and the compound which is used.

In practice, the compounds are advantageously applied in the case of foliar application in the range of concentration from 1 to 10000 ppm, and preferably 1 to 500 ppm. The compounds of the invention are advantageously applied to a locus to be treated at a dose within the range of 5 g/ha to 10 kg/ha, preferably from 10 g/ha to 1 kg/ha, and still more preferably from 50 to 500 g/ha. This is true for foliar applications to cropping area as well as to non crop area.

In the case of soil applications where the active ingredient is supposed to substantially penetrate the soil, higher doses may be advisable and may lie in the range from 0.01 to 100 kg/ha, preferably 0.2 to 20 kg/ha. More preferably an effective rate range of the active compound is from about 0.01 kg/ha to about 2 kg/ha.

Fungal diseases is understood to mean the diseases caused by phytopathogenic fungi and especially those of the family of the Oomycetes, Ascomycetes and Basidiomycetes.

The compounds of formula (I) show good control effects on plant diseases such as:

rice blast (*Pyricularia oryzae*), rice sheath blight (*Rhizoctonia solani*), rice brown spot (*Cochliobolus miyabeanus*), powdery mildew (*Erysiphe graminis*), septoria disease (*Septoria tritici* and *Septoria nodorum*), helminthosporiose (*Pyrenophora teres*), brown rust (*Puccinia recondita*), oat crown rust (*Puccinia coronata*), eye spot (*Pseudocercosporella herpotrichoides*), yellow rust (*Puccinia striiformis*), on various host plants such as cereals, including barley, wheat, oat, etc., potato and tomato late blight (*Phytophthora infestans*) and late blight of other crops, downy mildew of various plants such as cucumber downy mildew (*Pseudoperonospora cubensis*), grape downy mildew (*Plasmopara viticola*); apple scab (*Venturia inaequalis*); apple leaf spot (*Alternaria mali*); Japanese pear black spot (*Alternaria kikuchiana*); citrus melanose (Diaporthe citri); radish leaf spot (*Alternaria brassicae*); beet leaf spot (*Cercospora beticola*); cucumber powdery mildew (*Erysiphe cichoracearum*); bean rust (*Uromyces appendiculatus*).

The invention also provides a method for the for the control of arthropods, especially insects or mites, and of nematodes, helminths or protozoan pests at a locus which method comprises the application or administration of an effective amount of a compound of formula (I).

The compounds of this invention are useful in the control via foliar application or systemic action of other pests arthropods, especially insects, which feed on the above ground portions of plants. Control of foliar pests may additionally comprise an application to the plant roots or plant seeds with subsequent systemic translocation to the above ground portions of the plants.

The compounds of this invention may be useful to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests. The invention, as previously described, provides methods of control of pests via application or administration of an effective amount of compounds of formula (I) at a locus which comprises treatment of the locus.

The practical use for the control of arthropods, especially insects or mites, or nematode pests of plants, a method, for example, comprises applying to the plants or to the medium in which they grow an effective amount of a compound of the invention.

Methods of control of pests also comprise the application to or treatment of the foliage of plants to control arthropods, especially fungi, insects or mites, or nematodes attacking the aerial parts of the plants. In addition, methods of control of pests by the invention compounds are provided to control pests which attack or feed on parts of the plant remote from the point of application, e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, of ornamentals, or of plantation or forest trees, for example: cereals (such as maize, wheat, rice, or sorghum), cotton, tobacco, vegetables (such as beans, cole crops, curcurbits, lettuce, onions, tomatoes or peppers), field crops (such as potatoes, sugar beets, ground nuts, soybeans, or oil seed rape), sugar cane, grassland or forage crops (such as maize, sorghum, alfalfa), plantations (such as tea, coffee, cocoa, banana, palm oil, coconut, rubber, or spices), orchards or groves (such as of stone or pit fruit, citrus, kiwifruit, avocado, mango, olives or walnuts), vineyards, ornamental plants, flowers or vegetables or shrubs under glass or in gardens or parks, or forest trees (both deciduous and evergreen) in forests, plantations or nurseries. Cereals are preferred plants for the implementation of the process according to the invention.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which can spread or act as vectors of diseases in man or domestic animals. Such species comprise those hereinbefore mentioned as well as ticks, mites, lice, fleas, midges, and biting, myiasis or nuisance flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

The invention provides a pesticidal composition which comprises one or more compounds of formula (I) in association with a pesticidally acceptable carrier; the composition may also comprise a pesticidally acceptable surface active agent.

Another subject of the present invention is pesticidal fungicidal compositions, especially fungicidal compositions, containing, as active material(s), one or more compound(s) of formula (I), mixed with solid or liquid carriers which are acceptable in agriculture and surface-active agents which are also acceptable in agriculture. In particular, inert and conventional carriers and conventional surface-active agents can be used.

These compounds can be formulated into formulations usually adopted for fungicides, for example, dust, granule, wettable powder, flowable formula, etc.

In addition, these compounds can be used by mixing or applying together with other agrochemicals such as, for example, fungicides, insecticides, acaricides, herbicides, plant growth regulators, etc., fertilizers, soil conditioners, etc.

As carriers or diluents for formulation, there can be cited, for example, solid or liquid carriers which are usually usable.

As solid carriers, there can be cited, for example, clays represented by Kaolinites, montmorillonites, illites, polygroskites, etc., more precisely pyrophillite, attapulgite, sepiolite, kaolinite, bentonite, vermiculite, mica, talc, etc.; other inorganic substances such as gypsum, calcium carbonate, dolomite, diatom earth, magnesium lime, apatite, zeolite, silicic anhydride and synthetic calcium silicate; vegetable origin organic substances such as soybean meal, tobacco meal, walnut meal, wheat flour, sawdust, starch, crystalline cellulose, etc.; synthetic or natural high molecular compounds such as cumarone resins, petroleum resins, alkyd resins, poly(vinyl chloride), polyalkylene glycols, ketone resins, ester gum, copal gum and dammal gum; waxes such as carnauba wax and beewax; urea; etc.

As liquid carriers, there can be cited, for example, paraffin or naphthene hydrocarbons such as kerosine, mineral oil, spindle oil and white oil; aromatic hydrocarbons such as xylene, ethylbenzene, cumene, and methylnaphthalene; chlorinated hydrocarbons such as trichloroethylene, monochlorobenzene, o-chlorotoluene, etc.; ethers such as dioxane, tetrahydrofuran, etc.; ketones such as acetone, methyl ethyl ketone, diisobutyl ketone, cyclohexanone, acetophenone, isophorone, etc.; esters such as ethyl acetate, amyl acetate, ethylene glycol acetate, diethylene glycol acetate, dibutyl maleate, diethyl succinate, etc.; alcohols such as methanol, n-hexanol, ethylene glycol, diethylene glycol, cyclohexanol, benzyl alcohol, etc.; ether alcohols such as ethylene glycol ethyl ether, diethylene glycol ethyl ether, diethylene glycol butyl ether; polar solvents such as dimethylformamide, dimethyl sulfoxide, etc.; water; etc.

In addition, other auxiliaries can also be used for the purposes of emulsification, dispersion, wetting, spreading and binding of the active ingredients, adjustment of disintegrability, stabilization of the active ingredient, improvement of fluidity, corrosion protection, antifreezing, etc.

All the nonionic, anionic, cationic and amphoteric surfactants can be used as the surfactants, but usually used are nonionic and/or anionic ones.

Suitable nonionic surfactants include, for example, a compound obtained by adding ethylene oxide through polymerization to a higher alcohol such as lauryl alcohol, stearyl alcohol, oleyl alcohol, etc.; a compound obtained by adding ethylene oxide through polymerization to an alkylphenol such as isooctylphenol, nonylphenol, etc.; a compound obtained by adding ethylene oxide through polymerization to an alkylnaphthol such as butylnaphthol, octylnaphthol, etc.; a compound obtained by adding ethylene oxide through polymerization to a higher fatty acid such as palmitic acid, stearic acid, oleic acid, etc.; a higher fatty acid ester of a polyhydric alcohol such as sorbitan, etc. and a compound obtained by adding ethylene oxide through polymerization thereto; a compound obtained by adding through block polymerization ethylene oxide to propylene oxide; etc.

Suitable anionic surfactants include, for example, alkyl sulfate ester salts such as sodium lauryl sulfate, oleyl alcohol sulfate ester amine salts, etc.; alkylsulfonate salts such as sodium dioctyl sulfosuccinate, sodium 2-ethylhexenesulfonate, etc.; arylsulfonate salts such as sodium isopropylnaphthalenesulfonate, sodium methylenebisnaphthalenesulfonate, sodium ligninsulfonate, sodium dodecylbenzenesulfonate, etc.

Furthermore, there can also be used together for the fungicides of the present invention for the purpose of improving the performance of formulations and enhancement of fungicidal efficacy, higher molecular compounds such as casein, gelatin, albumin, glue, ligninsulfonate salts, alginate salts, carboxymethylcellulose, methylcellulose, hydroxyethylcellulose, polyvinylalcohol, etc.

The above carriers and various auxiliaries can appropriately be used alone or in combination, in accordance with purposes, taking the forms of formulations, sites for application, etc. into account.

The content of the effective ingredient in the fungicides of the present invention in various formulations thus obtained can be varied depending on formulations, but can, for example, be in the range of 0.1 to 99% by weight, preferably 1 to 60% by weight.

In case of wettable powder formulation. the fungicides contain, for example. usually 10 to 90% by weight of active ingredient(s), and the residual portion comprises a solid carrier, dispersing and wetting agents. If necessary, a protective colloid agent, and antifoaming agent, etc. are added thereto.

In case of granule formulation, the fungicides contain, for example, usually 1 to 35% by weight of active ingredient(s), and the residual portion comprises a solid carrier, a surfactant, etc. The active ingredient is either uniformly mixed with the solid carrier, or uniformly adheres to the surface of the solid carrier or is adsorbed on the surface, and the diameter of the granule can be in the range of about 0.2 to 1.5 mm.

In case of emulsified concentrate formulation, the fungicides contain, for example, usually 5 to 30% by weight of active ingredient(s), and approximately 5 to 20% of an emulsifier, and the residual portion consists of liquid carrier. If necessary, spreading and anti-corrosion agents, etc. can be added thereto.

In case of flowable formulation, the fungicides contain, for example, usually 5 to 50% by weight of active ingredient (s) and 3 to 10% by weight of dispersing and wetting agents, and the residual portion consists of water. If necessary, a protective colloid agent, an antiseptic agent, an antifoaming agent etc. are added thereto.

The hydroximic acid derivatives of the present invention can be used directly or after being formulated into various forms described above.

The following examples are given in order to illustrate the compounds, compositions and processes according to the present invention, and cannot be construed to limit said invention. Biological examples are illustrating the method of use of the invention. In these examples, the compounds were numbered according to the table above. When the stereochemistry of the structure was known, it has been indicated, using the number of the compound followed by the letters E or Z to indicate first the geometry of the C=G double bond, and then the geometry of the hydroximic group. When a stereoisomer was isolated but its stereochemistry was not yet precisely identified, the compounds are identified by the number corresponding to the chemical formula followed by a small letter (a or b), or by the letters MP or LP which mean more polar and less polar refering to Thin Layer Chromatography.

EXAMPLE 1

Compound No. 2

(Preparation of N-benzyloxyformamide by scheme 2 and application of method A):

O-benzylhydroxylamine (4.63 g, 37 mmol) was dissolved into 89% formic acid (80 ml), and 30 ml of acetic anhydride was added dropwise thereto with keeping the temperature at 50 to 60° C. After adding acetic anhydride, the solution was stirred for 2 hours at room temperature. The organic layer was rinsed and dried, and the solvent was evaporated. The residue was then purified with silica gel chromatography to obtain 3.05 g of N-benzyloxyformamide (yield: 60%). The proton NMR spectrum of the compound is 4.82 bs, 4.93 bs (2H); 7.20–7.47 m (5H); 7.93 bs, 8.30 bs (1H) (solvent: $CDCl_3$).

N-benzyloxyformamide (1 g, 6.6 mmol) was dissolved into 15 ml of dimethylformamide. After cooling down to 0° C., 60% sodium hydride (0.34 g, 8.5 mmol) was added thereto, and stirred for 30 minutes at the same temperature. The reaction solution was further stirred for 40 minutes at room temperature, and added dropwise thereto methyl 2-(2-bromomethyl)phenyl-2-methoxyiminoacetate (2.85 g, 6.6 mmol) dissolved in dimethylformamide (8 ml).

After stirring for one day at room temperature, the reaction solution was poured into 20 ml of water, and there was extracted with ethyl acetate. The organic layer was rinsed with water, and dried. After the solvent was removed by evaporation, the residue was purified with silica gel chromatography to obtain 0.40 g of methyl 2-(2-benzyloxyiminomethyloxymethylphenyl)-2-methoxyiminoacetate (yield: 14%). The proton NMR spectrum of the compound is 3.81s(3H),4.01s(3H),4.85s (2H),5.01s(2H),6.48s(1H),7.12–7.19m(1H),7.23–7.52m (8H).

EXAMPLE 2

Compound No. 4 (E, Z)

(Preparation of N-benzyloxyacetamide by scheme 3 and application of method A)

60% sodium hydride (11.68 g, 0.292 mol) was added to a dimethyliformamide solution (200 ml) of acetohydroxamic acid (21.9 g, 0.292 mol) with cooling in an ice bath. After stirring for 1 hour at room temperature, benzylbromide (50 g, 0.292 mol) was added thereto and allowed to react for 24 hours at room temperature. The reaction solution was poured into 500 ml of water. and extracted with ethyl acetate. The organic layer was rinsed with water and dried. After removing the solvent by evaporation, the residue was purified with silica gel chromatography to obtain 31.3 g of N-benzyloxyacetamide (yield: 65%). The proton NMR spectrum of the compound is 1.85 s (3H); 4.89 bs (2H); 7.37 s (5H); 8.30 bs, 8.81 bs (1H) (solvent: $CDCl_3$).

A solution of N-benzyloxyacetamide (1.65 g, 10 mmol) in 10 ml of dimethylformamide was cooled down in an ice bath, 60% sodium hydride (0.4 g, 10 mmol) was added thereto, and stirred for 10 minutes. After adding dropwise 20 ml of dimethylformamide solution of 2-bromomethylphenyl-3-methoxypropenoate (2.85 g, 10 mmol), the solution was allowed to react for 15 hours at room temperature. After completion of the reaction, the reaction solution was poured into 200 ml of water, and extracted with ethylacetate. The organic layer was rinsed with water and dried. After removing the solvent by evaporation, the residue was purified with silica gel chromatography to obtain 0.34 g of methyl 2-[2-(1-benzyloxyiminoethyl) oxymethylphenyl]-3-methoxypropenoate (yield: 9.2%). The proton NMR spectrum is 1.79 s (3H); 3.67 s (3H); 3.77 s (3H); 5.01 s (2H); 5.04 s (2H); 7.10–7.50 m (9H); 7.57 s (1H) (solvent: $CDCl_3$).

EXAMPLE 3

Compound No. 7(E, Z)

(Preparation of N-benzyloxypropionamide by scheme 3 and application of method A):

A mixture of propionylhydroxamic acid (4.5 g, 50 mmol), benzylbromide (8.55 g, 50 mmol), potassium carbonate (7.6 g, 55 mmol) and acetonitrile (50 ml) was stirred for 50 hours at room temperature. After completion of the reaction, the reaction solution was filtered, the solvent was removed by evaporation, and the residue was purified with silica gel chromatography to obtain N-benzyloxypropionamide (8.5 g, yield: 100%). The proton NMR spectrum of this compound is 1.14 t (3H); 2.08 b (2H); 4.89 b (2H); 7.38 s (5H); 8.10 b (1H) (Solvent: $CDCl_3$).

A mixture of N-benzyloxypropionamide (1.8 g, 10 mmol), 2-bromomethylphenyl-3-methoxypropenoate (2.85 g, 10 mmol), potassium carbonate (1.66 g, 12 mmol), 4-N,N-dimethyl-aminopyridine (0.1 g) and acetonitrile (20 ml) was heated with reflux for 7 hours. After completion of the reaction, the reaction solution was filtered, the solvent was removed by evaporation, and the residue was purified with silica gel chromatography to obtain methyl 2-[2-{(1-benzyloxyiminopropyl)oxymethyl}phenyl]-3-methoxypropenoate (1.00 g, yield: 26%). The proton NMR Spectra: 1.04 t (3H); 2.21 q (2H); 3.67 s (3H); 3.73 s (3H); 5.01 s (2H); 5.10 s (2H); 7.13–7.45 m (9H); 7.54 s (1H) (Solvent: $CDCl_3$).

EXAMPLE 4

(Scheme 4)

18 g (0.1 mol) of O-benzylpropiohydroxamic acid and 40 g (0.1 mol) of Lawesson reagent are stirred 1h30 in 200 ml of THF (abbreviation for tetrahydrofurane) at room temperature. 500 ml of 1.2N ammonia are added. The aqueous phase is extracted with ether. The aqueous phase is then neutralised with concentrated HCl, extracted with ether, dried over Magnesium sulfate and the solvents evaporated to give 12.5 g (64%) of a colorless oil which was used without further purification; NMR: 1.20t (3H), 2.45 q(2H), 4.3 bs(1H), 5.15s(2H), 7.20–7.45m(5H).

Similarly compounds were prepared according to the following table (Rf is a known measure of migration ability of the compounds in thin layer chromatography):

| | |
|---|---|
| O— benzylthioformohydroxamic acid | 30%, liquid, Rf = 0.8 (ethyl acetate/hexane 20/80) |
| O— benzylthioacetohydroxamic acid | 27%, liquid, Rf = 0.8 (ethyl acetate/hexane 20/80) |
| O— benzylformothioisopropioxamic acid | 37%, liquid, Rf = 0.9(ethyl acetate/hexane 20/80) |

EXAMPLE 5

(Method A; W=S)

Compound No. 634a

A mixture of N-benzyloxythiopropionamide (1.2 g, 6 mmol) prepared as above, 2-bromomethylphenyl-3- methoxypropenoate (1.7 g, 6 mmol) and potassium carbonate (1 g, 7 mmol) was stirred overnight at room temperature. The reaction mixture was filtered, the solvent was removed by evaporation, and the residue was purified with silica gel chromatography to obtain methyl 2-[2-{(1-benzyloxyiminopropyl)thiomethyl}phenyl]-3-methoxypropenoate (1.6 g, yield: 67%). The proton NMR Spectra: 1.12 t (3H); 2.36 q (2H); 3.67 s (3H); 3.77 s (3H); 3.95 s (2H); 5.12 s (2H); 7.15–7.50 m (9H); 7.59 s (1H) (Solvent: CDCl$_3$).

Other compounds were prepared in a similar manner to Examples 1 to 5. They are shown in Table 2.

TABLE 2

| Comp ose N° | NMR spectrum based on proton (ppm) and made in CDCl$_3$ solution. Meanings: s = singlet; d = doublet; t = triplet; q = quartet and m = multiplet. |
|---|---|
| 4 | 1.79s(3H), 3.67s(3H), 3.77s(3H), 5.01s(2H), 5.04s(2H), 7.10–7.50m(9H), 7.57s(1H) |
| 5(EZ) | 1.82s(3H).3.83s(3H), 4.01s(3H), 5.00s(2H), 5.02s(2H), 7.13–7.49m(9H) |
| 16 | 1.56d(3H), 1.75s(3H), 3.68s(3H), 3.79s(3H), 5.05–5.10m(3H), 7.12–7.40m(9H), 7.58s(1H) |
| 17 | 1.51d, 1.55d(3H), 1.77s(3H), 3.84s3.87s(3H), 3.95s4.03s(3H), 4.7–4.9m(1H), 5.02–5.10m(2H), 7.14–7.53m(9H) |
| 8(EZ) | 1.05t(3H), 2.14q, 2.51q(2H), 3.82s(3H), 3.98s(3H), 4.99s(2H), 5.08s(2H), 7.16–7.47m(9H) |
| 1 | 3.67s(3H), 3.77s(3H), 4.94s(2H), 5.01s(2H), 6.49s(1H), 7.20–7.48m(9H), 7.58s(1H) |
| 7(EZ) | 1.04t(3H), 2.21q(2H), 3.67s(3H), 3.73s(3H), 5.01s(2H), 5.10s(2H), 7.13–7.45m(9H), 7.54s(1H) |
| 2 | 3.81s(3H), 4.01s(3H), 4.89s(2H), 5.01s(2H), 6.48s(1H), 7.12–7.19m(1H), 7.23–7.52m(8H) |
| 148 | 1.79s(3H), 2.35s(3H), 3.67s(3H), 3.75s(3H), 5.04s(2H), 5.04s(2H), 7.00–7.50m(8H), 7.57s(1H) |
| 167 | 1.82s, 2.19s(3H), 2.32s, 2.36s(3H), 3.83s, 3.86s(3H), 4.02s(3H), 4.69s, 4.97s(2H), 5.02s, 5.15s(2H), 7.01–7.53m(8H) |
| 154 | 1.78s(3H), 2.35s(3H), 3.67s(3H), 3.77s(3H), 4.97s(2H), 5.03s(2H), 7.08–7.20m(3H), 7.25–7.35m(4H), 7.43–7.49m(1H), 7.57s(1H) |
| 173 | 1.81s, 2.16s(3H), 2.33s, 2.34s(3H), 3.83s, 3.86s(3H), 4.01s(3H), 4.68s, 4.95s(2H), 5.01s, 5.14s(2H), 7.10–7.19m(3H), 7.24–7.57m(5H) |
| 142(EZ) | 1.81s(3H), 2.39s(3H), 3.67s(3H), 3.76s(3H), 5.02s(2H), 5.04s(2H), 7.09–7.41m(7H), 7.45–7.56m(1H), 7.56s(1H) |
| 161 | 1.83s(3H), 2.38s(3H), 3.82s(3H), 4.00s(3H), 5.01s(4H), 7.07–7.53m(8H) |
| 141 | 1.82s(3H), 3.68s(3H), 3.79s(3H), 5.07s(2H), 5.13s(2H), 7.10–7.41m(6H), 7.46–7.57m(2H), 7.59s(1H) |
| 160 | 1.84s(3H), 3.84s(3H), 4.02s(3H), 5.05s(2H), 5.11s(2H), 7.12–7.30m(3H), 7.31–7.59m(5H) |
| 144 | 1.80s(3H), 3.68s(3H), 3.78s(3H), 3.83s(3H), 5.06s(2H), 5.08s(2H), 6.83–7.00m(2H), 7.10–7.16m(1H), 7.22–7.44m(4H), 7.48–7.55m(1H), 7.57s(1H) |
| 163 | 1.82s(3H), 3.83s(3H), 3.84s(3H), 4.02s(3H), 5.04s(2H), 5.07s(2H), 6.81–7.00m(2H), 7.11–7.58m(6H) |
| 143(EZ) | 1.82s(3H), 3.67s(3H), 3.79s(3H), 5.08s(2H), 5.23s(2H), 7.13–7.18m(1H), 7.23–7.31m(3H), 7.53–7.68m(4H), 7.59s(1H) |
| 149(EZ) | 1.80s(3H), 3.68s(3H), 3.90s(3H), 5.04s(2H), 5.05s(2H), 7.13–7.15m(1H), 7.30–7.68m(7H), 7.59s(1H), |
| 8(ZE) | 1.10t(3H), 2.46q(2H), 3.85s(3H), 3.96s(3H), 4.94s(2H), 5.18s(2H), 7.25–7.41m(8H), 7.40d(1H) |
| 8(ZZ) | 1.06t(3H), 2.17q(2H), 3.88s(3H), 5.03s(2H), 5.44s(2H), 7.26–7.43m(8H), 7.63d(1H) |
| 10(EZ) | 1.06d(6H); 2.42h(1H); 3.64s(6H); 4.97s(2H); 5.21s(2H); 7.00–7.47m(9H); 7.48s(1H) |
| 659(EZ) | 0.50–0.60m(2H); 0.62–0.70m(2H); 1.35m(1H); 3.62s(6H); 4.96s(2H); 5.20s(2H); 7.10–7.55m(9H); 7.51s(1H) |
| 634a | 1.12t(3H); 2.36q(2H); 3.67s(3H); 3.77s(3H); 3.95s(2H); 5.12s(2H); 7.15–7.50m(9H); 7.59s(1H) |
| 634b | 1.09t(3H); 2.43q(2H); 3.69s(3H); 3.78s(3H); 4.02bs(2H); 5.09s(2H); 7.05–7.40m(9H); 7.56s(1H). |

TABLE 2-continued

| Comp ose N° | NMR spectrum based on proton (ppm) and made in CDCl$_3$ solution. Meanings: s = singlet; d = doublet; t = triplet; q = quartet and m = multiplet. |
|---|---|
| 633a | 2.04s(3H); 3.66s(3H); 3.77s(3H); 3.95s(2H); 5.10s(2H); 7.05–7.50m(9H); 7.59s(1H); MP: 80° |
| 633b | 1.89s(3H); 3.67s(3H); 3.78s(3H); 3.81s(2H); 5.11s(2H); 7.05–7.45m(9H); 7.58s(1H) |
| 25 | 1.09d(6H); 2.58h(1H); 3.67s(3H); 3.75s(3H); 3.98s(2H); 5.13s(2H); 7.00–7.40m(9H); 7.57s(1H) |
| 632 | 3.66s(3H); 3.78s(3H); 3.88s(3H); 5.12s(2H); 5.29s(1H); 7.10–7.45m(9H); 7.59s(1H) |
| 637a | 1.11t(3H); 2.35q(2H); 3.81s(3H); 3.92s(2H); 4.02s(3H); 5.12s(2H); 7.10–7.50m(9H); MP: 53° |
| 637b | 1.07t(3H); 2.42q(2H); 3.86s(3H); 3.95s(2H); 4.03s(3H); 5.08s(2H); 7.10–7.45m(9H) |

EXAMPLE 6

Preparation of Compound 7 with E, E double bond configurations: (7(EE) METHOD C Compound 7(EZ) (266 g) were dissolved in toluene (2 l.) and heated to reflux for 2 hours. After evaporation of the solvent, the residue was purified by silica gel chromatography to provide the compound 7(E,E) (72 g) as a gum. The following compounds were prepared according to the same way. In some cases UV irradiation or acetic acid catalysis were required.

| compound No | NMR spectrum as defined here above. |
|---|---|
| 9(E, E) | 1.05t(3H); 2.14q(2H); 2.81d(3H); 3.89s(3H); 4.97s(2H); 5.77s(2H); 6.71bd(1H); 7.16–7.20m(1H); 7.30–7.45m(8H) |
| 5(E, E) | 1.92s(3H), 3.84s(3H), 4.00s(3H), 4.86s(2H), 4.93s(2H), 7.18–7.43m(9H) |
| 142(E, E) | 2.22s(3H), 2.66s(3H), 3.95s(3H), 4.03s(3H), 5.15s(2H), 5.23s(2H), 7.40–7.80m(8H), 7.82s(1H) |
| 143(E, E) | 1.99s(3H), 3.66s(3H), 3.73s(3H), 4.85s(2H), 5.15s(2H), 7.13–7.17m(1H), 7.22–7.43m(5H), 7.52s(1H), 7.52–7.70m(2H) |
| 149(E, E) | 1.97s(3H), 3.67s(3H), 3.74s(3H), 4.84s(2H), 4.98s(2H), 7.13–7.16m(1H), 7.29–7.62m(7H), 7.53s(1H) |
| 8E, E) | 1.04t(3H), 2.38q(2H), 3.83s(3H), 4.00s(3H), 4.84s(2H), 4.91s(2H), 7.15–7.20m(1H), 7.22–7.45m(7H) |
| 7(E, E) | 1.05(t, 3H), 2.40(q, 2H), 3.66(s, 3H), 3.73(s, 3H), 4.85(s, 2H), 4.92(2,H), 7.10–7.50(m, 9H), 7.55(s, 1H) |
| 16(E, E) | 1.50(d, 3H), 1.97(s, 3H), 3.65(s, 3H), 3.68(s, 3H), 4.80(s, 2H), 5.03(q, 1H), 7.05–7.45(m, 9H), 7.48(s, 1H) |
| 10(E, E) | 1.03d(6H); 3.30h(1H); 3.64s(3H); 3.66s(3H); 4.84s(2H); 4.91s(2H); 7.05–7.45m(9H); 7.51s(1H) |
| 659(EE) | 0.65–0.75m(2H); 0.85–0.95m(2H); 2.20–2.35m(1H); 3.68s(3H); 3.75s(3H); 4.81s(2H); 4.98s(2H); 7.10–7.45m(9H); 7.52s(1H) |

EXAMPLE 7

Preparation of compounds 642 and 651 (W=SO, SO2) METHOD D Methyl 3-methoxy-2-(2-(N-benzyloxy) acetimidoylsulfinyl methyl phenyl)-acrylate and methyl 3-methoxy-2-(2-(N-benzyloxy)acetimidoyl sulfonyl methyl phenyl)-acrylate Methyl 3-methoxy-2-(2-(N-benzyloxy) acetimidoylthiomethylphenyl)-acrylate (0.5 g, 1.6 mmol) were reacted with 0.39 g (1.6 mmol) of metachloroperbenzoic acid in methylene chloride 4 days at room temperature. After work-up and column chromatography (20 AcOEt-80 Hexane) were isolated 0.05 g and 0.05 g of the compounds 642 and 651 as oils.

| | |
|---|---|
| 642 | 1.94s(3H); 3.68s(3H); 3.76s(3H); 4.43s(2H); 5.25s(2H); 7.15–7.45m(9H); 7.56s(1H) |
| 651 | 2.04s(3H); 3.66s(3H); 3.72s(3H); 3.97s(2H); 5.11s(2H); 7.10–7.40m(9H); 7.55s(1H) |

EXAMPLE 8

METHOD B. Compound No. 3

Methyl 2-(2-benzyloxyiminomethyloxymethylphenyl)-2-methoxyiminoacetate) (compound No. 2) (200 mg. 0.6 mmol) was dissolved into 8 ml of methanol, an aqueous solution of 40% methylamine (230 mg, 2.9 mmol) was added thereto. After stirring for 1 day, water was added to the reaction solution, methanol was removed by evaporation, and there was extracted with ethyl acetate. The organic layer was rinsed with water and dried. After removing the solvent by evaporation, the residue was purified with silica gel chromatography to obtain 0.18 g of N-methyl 2-(2-benzyloxyiminomethyloxymethylphenyl)-2-methoxyiminoacetamide (Compound No. 3; yield: 90%). The proton NMR spectrum of the compound is 2.81 s (3H); 3.89 s (3H); 4.91 s (2H); 5.00 s (2H); 6.52 s (1H): 6.82 bd(1H); 7.15–7.21 m (1H); 7.23–7.47 m (8H) (solvent: $CDCl_3$).

The compounds prepared by the same methods described in Preparation Examples above are shown in Table 3.

TABLE 3

| compound No | NMR spectrum as defined here above |
|---|---|
| 9 | 1.05t(3H), 2.14q, 2.41q(2H), 2.82d(3H), 3.90s, 3.96s(3H), 4.01s(3H), 4.78s, 5.01s(2H), 7.20–7.55m(9H) |
| 3 | 2.81s(3H), 3.89s(3H), 4.91s(2H), 5.00s(2H), 6.52s(1H), 6.82bd(1H), 7.15–7.21m(1H), 7.23–7.47m(8H) |
| 192 | 1.82s, 2.06s(3H), 2.35s, 2.36s(3H), 2.79d, 2.82d(3H), 3.91s, 4.01s(3H), 4.72s, 4.94s(2H), 4.99s, 5.02s(2H), 6.17bd(1H), 7.13–7.54m(8H) |
| 179 | 1.84s(3H), 2.85s(3H), 3.91s(3H), 5.06s(2H), 5.11s(2H), 6.81bd(1H), 7.15–7.29m(3H), 7.31–7.53m(5H) |
| 182 | 1.84s(3H), 2.82s(3H), 3.84s(3H), 3.86s(3H), 5.04s(2H), 5.05s(2H), 6.82–6.99m(3H), 7.18–7.46m(6H) |
| 640a | 1.11t(3H); 2.35q(2H); 2.89d(3H); 3.94s(5H); 5.12s(2H); 6.7–6.85bs(1H); 7.10–7.50m(9H); Melting point: 83° |
| 640b | 1.08t(3H); 2.42q(2H); 290d(3H); 3.94s(5H); 5.08s(2H); 6.65–6.75bs(1H); 7.10–7.45m(9H) |

Several formulations of the active ingredients of the invention were made according to the following examples. All "parts" are by weight unless otherwise indicated.

Formulation Example 1
(Emulsified Concentrate Formula)

| | |
|---|---|
| Compound No. 11 | 10 parts |
| Xylene | 45 parts |
| Calcium dodecylbenzenesulfonate | 7 parts |
| Polyoxyethylene styrylphenyl ether | 13 parts |
| Dimethylformamide | 25 parts |

The above mixture was mixed and dissolved homogeneously to obtain 100 parts of emulsified concentrate formula.

Formulation Example 2
(Wettable Powder Formula)

Compound No. 16 20 parts

Diatomaceous earth 70 parts

Calcium lignosulfonate 5 parts

Condensation product of naphthalenesulfonic acid-formalin 5 parts

The above mixture was mixed and ground to obtain 100 parts of wettable powder formula.

Formulation Example 3
(Granule Formula)

| | |
|---|---|
| Compound No. 43 | 5 parts |
| Bentonite | 50 parts |
| Talc | 42 parts |
| Sodium lignosulfonate | 2 parts |
| Polyoxyethylenealkylaryl ether | 1 parts |

The above mixture was mixed, kneaded with adding appropriate amount of water, and granulated with a granulator to obtain 100 parts of granule formula.

Biological Example 1
(Control Test on Rice Blast)

Rice (cultivar Koshihikari) seeds were sown in a plastic cup and kept in a greenhouse for 3 weeks. Emulsified concentrates according to formulation example 1 were diluted with water to 200 ppm, and sprayed allover the surface of rice plant. After one day from spraying, a further spraying was made with a suspension solution of spores of rice blast. The plants were then kept for one day in a humidified dark chamber at 25° C., and then transfered to a greenhouse. After 7 days from this second spraying, average disease spots were counted per leaf, and compared to those of non-sprayed plot.

Under these conditions a good (at least 80%) or total protection was observed with the compounds: 2, 3, 4, 5(EZ), 5(EE), 7(EE), 8(EE), 9, 16, 17, 141, 142(EZ), 142(EE), 143(EZ), 143(EE), 144, 148, 149(EZ), 149(EE), 154, 160, 161, 163, 173, 179, 182.

Biological Example 2
(Control Test on Rice Sheath Blight)

Rice (Cultivar Koshihikari) seeds were sown and kept in a greenhouse for 4–6 weeks. At the time when the 5th leaf was spread, emulsified concentrates according to formulation example 1 were diluted with water to 200 ppm, and sprayed over the plants (25 ml per 6 plants). After air drying, the mycelium of rice sheath blight was inoculated to rice seedlings at the bottom of the plants. These plants were transfered into a chamber humidified at 100% and 28° C. After 3 days, average disease spots were counted per leaf, and control effects were assessed in accordance with the same criteria as described in Test Example 1. The test results are shown in Table 4.

Under these conditions a good (at least 80%) or total protection was observed with the compounds: 5(EZ), 8(EE), 142(EZ), 143(EE), 144, 160, 173, 182

Biological Example 3

In vivo test on *Puccinia recondita* responsible for brown rust of wheat:

Aqueous suspensions of the active material to be tested, having the following composition, were prepared, by fine milling the following mixture:

active material: 60 mg acetone: 5 ml surface-active agent Tween 80 (oleate of polyoxyethylenated derivative of sorbitan) diluted to 10% in water: 0.3 ml made up to 60 ml with water.

These aqueous suspensions were then diluted with water to obtain the desired concentration of active material.

Wheat, (variety Scipion), seeded on a 50/50 peat/pozzolana substrate in a small pot and maintained at 12° C. was treated at the 10 cm-high stage by spraying with the above aqueous suspension.

After 24 hours, an aqueous suspension of spores (100 000 sp/cm$^3$) was sprayed on the wheat: this suspension was obtained from infected seedlings. The wheat was then placed for 24 hours in an incubation cell at approximately 20° C. and at 100% relative humidity, and then for 7 to 14 days at 60% relative humidity.

Visual observation of the condition of the seedlings was carried out between the 8th and 15th day after infection, by comparison with an untreated control.

Under these conditions, at a dose of 0.1 g/l, a good (at least 75%) or total protection was observed with the following compounds:1, 3, 4, 5(EE), 7(EE), 8(EZ), 8(EE), 8(ZE), 8(ZZ)9 (EE), 25, 16(EE), 17, 141, 14(EZ), 142(EE) 148, 149(EE), 154, 167, 179, 633, 634, 637, 640, 651

A dose of 1 g/l in the conditions of this test corresponds to a dose expressed in terms of g/ha of the order of 1 kg/ha.

Biological Example 4

In vivo test on *Septoria tritici* responsible for septoria disease of wheat:

Aqueous suspensions, with a concentration of 1 g/l, of the active material tested were obtained by milling 60 mg of the latter with acetone (5 ml) and a surface-active agent which was oleate of Tween 80 (diluted to 10% ; 0.3 ml), and then the volume was adjusted to 60 ml with water.

These aqueous suspensions were then diluted with water to obtain the desired concentration of active material.

Wheat seedlings (variety Scipion), seeded on a 50/50 peat/pozzolana substrate and grown under glass at a temperature of 10–12° C., are treated at the 1 leaf stage (size of approximately 10 cm) by spraying with the active material suspension described above.

Seedlings, used as controls, were treated by spraying with an aqueous solution which does not contain the active material.

24 hours after treatment, the seedlings were infected by spraying with an aqueous suspension of spores (500 000 sp/ml) harvested from a 7-day old culture.

After infection, the seedlings were placed at 18° C. in a humid atmosphere. Assessment was carried out 20 days after infection, by comparison with the control seedlings.

Under these conditions, at a dose of 0.1 g/l, a good (at least 75%) or total protection was observed with the compounds: 2, 3, 5 (EE), 7(EZ), 7(EE), 8(EZ), 8(EE), 8(ZE), 8(ZZ), 9(EE), 10(EZ), 10(EE), 25, 16(EE), 17, 142(EZ), 142(EE), 143(EZ), 143(EE), 149(EZ), 149(EE), 154, 167, 632, 633, 634, 637, 640, 651, 659(EE), 659(EZ)

A dose of 1 g/l in the conditions of this test corresponds to a dose expressed in terms of g/ha of the order of 1 kg/ha.

Test Example 5

In vivo test on *Septoria nodorum* responsible for septoria disease of wheat:

Aqueous suspensions, with a concentration of 1 g/l, of the active material tested were obtained by milling 60 mg of the latter with acetone (5 ml) and Tween 80 (diluted to 10%: 0.3 ml), and then the volume was adjusted to 60 ml with water.

These aqueous suspensions were then diluted with water to obtain the desired concentration of active material.

Wheat seedlings (variety Scipion), seeded on a 50/50 peat/pozzolana substrate and grown under glass at a temperature of 10–12° C., were treated at the 1 leaf stage (size of approximately 10 cm) by spraying with the active material suspension described above.

Seedlings, used as controls, were treated by spraying with an aqueous solution without the active material.

24 hours after treatment, the seedlings were infected by spraying with an aqueous suspension of spores (500 000 sp/ml) harvested from a 7-day old culture.

After infection, the seedlings were placed at 18° C. in a humid atmosphere. Assessment was carried out 20 days after infection, by comparison with the control seedlings.

Under these conditions, at a dose of 0.1 g/l, a good (at least 75%) or total protection was observed with the compounds: 4, 5(EE), 7(EZ), 7(EE), 8(EZ), 8(EE), 8(ZE), 8(ZZ), 9(EE), 10(EZ), 10(EE), 25, 16(EE), 17, 141, 142(EZ), 142(EE), 143(EZ), 143(EE), 149(EZ), 149(EE), 154, 179, 632, 633, 634, 637, 640, 642, 651, 659(EE), 659(EZ)

A dose of 1 g/l in the conditions of this test corresponds to a dose expressed in terms of g/ha of the order of 1 kg/ha.

Test Example 6

In vivo test on *Erisyphe graminis* var. hordei, responsible for powdery mildew of barley:

Aqueous suspension of the active material to be tested, having the following composition, were prepared, by fine milling the active material (60 mg) and acetone (5 ml) and Tween 80 (diluted to 10% in water; 0.3 ml) and then made up to 60 ml with water.

These aqueous suspensions were then diluted with water to obtain the desired concentration of active material.

Barley, (variety Express), seeded on a 50/50 peat/pozzolana substrate in a small pot and maintained at 12° C., was treated at the 10 cm-high stage by spraying with the above aqueous suspension.

After 24 hours, inoculation by dusting dry conidia was carried out on the plants.

The barley was then placed 10 days at 60% relative humidity and 20° C. Assessment was carried out 10 days after infection by comparison with an untreated control.

Under these conditions, at a dose of 0.1 g/l, a good (at least 75%) or total protection was observed with the following compounds: 4, 5(EE), 7(EE), 8(EZ), 8(EE), 8(ZE), 8(ZZ), 9(EE), 10(EZ), 10(EE), 25, 16(EE), 141, 142(EZ), 142(EE), 143(EZ), 143(EE), 149(EZ), 148, 149(EZ), 149 (EE), 154, 179, 632, 634, 637, 640, 642, 659(EE), 659(EZ)

A dose of 1 g/l in the conditions of this test corresponds to a dose expressed in terms of g/ha of the order of 1 kg/ha.

Test Example 7

In vivo test on *Dreschlera teres* responsible for barley net blotch:

Aqueous suspension of the active material to be tested, having the following composition, were prepared, by fine milling the active material (60 mg) and acetone (5 ml) and Tween 80 (diluted to 10% in water; 0.3 ml) and then made up to 60 ml with water.

These aqueous suspensions were then diluted with water to obtain the desired concentration of active material.

Barley (variety Express), seeded on a 50/50 peat/pozzolana substrate in a small pot and maintained at 12° C., was treated at the 10 cm-high stage by spraying with the above aqueous suspension.

After 24 hours, an aqueous suspension of spores (100 000 sp/cm$^3$) was sprayed on the barley; this suspension was obtained from infected seedlings. The wheat was then placed for 24 hours in an incubation cell at approximately 20° C. and at 100% relative humidity, and then for 7 to 10 days at 60% relative humidity. Assessment of the condition of the seedlings was carried out between the 8th and 11th day after infection, by comparison with an untreated control.

Under these conditions, at a dose of 0.1 g/l, a good (at least 75%) or total protection was observed with the following compounds:1, 3, 4, 5(EE), 7(EE), 8(EZ), 8(EE), 8(ZE), 8(ZZ)9 (EE), 10(EE), 16(EE), 17, 142(EZ), 142(EE), 143(EZ), 43(EE), 148, 149(EE), 154, 167, 632, 633, 634, 637, 640, 651, 659(EZ)

A dose of 1 g/l in the conditions of this test corresponds to a dose expressed in terms of g/ha of the order of 1 kg/ha.

Method of use of Arthropocidal Compounds

The following representative test procedures, using compounds of the invention, were conducted to determine the pesticidal use and activity of compounds of the invention against certain insects, including an aphid, a caterpillars, a fly, a cockroach, and a corn rootworm. The specific species tested were as follows:

| GENUS, SPECIES | COMMON NAME |
|---|---|
| *Aphis gossypii* | (cotton aphid) |
| *Spodoptera eridania* | southern armyworm |
| *Musca domestica* | house fly |
| *Periplaneta americana* | American cockroach |
| *Diabrotica undecimpunctata* | southern corn rootworm |

Formulations

The test compounds were formulated for use according to the following methods.

For aphids, southern armyworm, and southern corn rootworm a solution or suspension was prepared by adding the test compound to a solution of dimethylformamide, acetone, emulsifiers which are alkylaryl polyether alcohols organic sulfonates, and water. The result was a 500 ppm concentration of the test compound.

For house fly tests, the water-acetone-DMF-emulsifier solution was adjusted with a 20% by weight aqueous solution of sucrose to provide a 250 concentration of the test compound.

For southern corn rootworm tests, the water-acetone-DMF-emulsifier solution was adjusted for a treatment rate of 6.75 ppm.

Test Procedures

The above formulated test compounds were then evaluated for their pesticidal activity at specified concentrations, in ppm (parts per million) by weight or in kg/ha (kilograms per hectare). The following procedures were used to evaluate a number of compounds within the scope of the invention.

Cotton aphid: Adult and nymphal stages of cotton aphid were reared on potted dwarf nasturtium or cotton plants, respectively. Plants infested with 100–150 aphids were wet to runoff with the 500 ppm test compound formulations. As an untreated control, a water-acetone-DMF-emulsifier solution containing no test compound was also applied wet to runoff to infested plants. The treated plants were stored for three days, after which the dead aphids were counted.

Southern armyworm: Bean leaves were wet to runoff with the 500 ppm test compound formulation. As an untreated control, a water-acetone-DMF-emulsifier solution containing no test compound was also applied wet to runoff to bean leaves. Five or six randomly selected second instar southern armyworm larvae were introduced into each plastic container with the dry treated leaves. The container was closed and left for five days. Larvae which were unable to move the length of the body, even upon stimulation by prodding, were considered dead.

House fly: Four to six day old adult house flies were used. The flies were immobilized by anesthetizing with carbon dioxide. A bait cup was prepared which contained the 250 test compound formulation/sucrose solution and absorbent cotton pad(s). As an untreated control, a water-acetone-DMF-emulsifier-sucrose solution containing no test compound was applied in a similar manner. The bait cup was introduced inside the cage prior to admitting 12–25 anesthetized flies. Mortality was assessed after 24 hours.

Southern corn rootworm: Corn seeds were placed in a glass jar and covered with dry sandy loam soil. The 500 ppm test compound was applied for a soil concentration of 6.75 ppm. As an untreated control, an aliquot of a water-acetone-DMF-emulsifier solution containing no text compound was applied in a similar manner. After incubating covered for 24 hours, the soil was mixed and inoculated with approximately 25 southern corn rootworm eggs. Eight days after infestation, mortality was assessed by Berlese funnel extraction.

American cockroach: Dog food pellets were added to jars containing 1–2 mls of the 500 ppm test formulation. As an untreated control, an aliquot of a water-acetone-DMF-emulsifier solution containing no test compound was applied in a similar manner. After 48 hours, roach nymphs were added to the jar. Contact and feeding mortality was assessed 1 and 5 days after infestation.

Test Results

The above procedures were used to evaluate a number of compounds within the scope of the invention. The following compounds in Table 4 were active against one or more insects described above up to 100% mortality.

TABLE 4

| CMPD. No. | Aphis gosspii | Spodoptera eridania | Musca domestica | Periplaneta americana | Diabrotica undecimpu nctata |
|---|---|---|---|---|---|
| 5(EZ) |  | X |  |  | X |
| 16 | X | X | X |  |  |
| 16(EE) |  | X |  | X |  |
| 8(EZ) |  | X | X |  |  |
| 9 |  | X | X | X | X |
| 9(EE) |  | X |  |  |  |
| 7(EZ) |  | X | X | X |  |
| 7(EE) |  | X | X | X |  |
| 142(EZ) |  | X | X | X |  |

What is claimed is:
1. A compound having the formula:

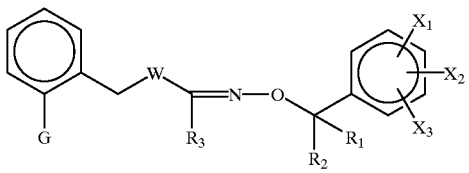

wherein:
G is $G_3$ or $G_4$ having the formula:

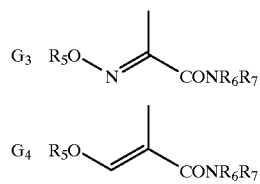

$X_1$, $X_2$ and $X_3$ are, independently:
  hydrogen or halogen;
  hydroxy, mercapto, nitro, thiocyanato, azido or cyano;
  alkyl, haloalkyl, cyanoalkyl, alkoxy, haloalkoxy, cyanoalkoxy, alkylthio, haloalkylthio, cyanoalkylthio, alkylsulfinyl, haloalkylsulfinyl, alkylsulfonyl or haloalkylsulfonyl, each alkyl or alkoxy being a lower radical;
  cycloalkyl, halocycloalkyl, alkenyl, alkynyl, alkenyloxy, alkynyloxy, alkenylthio or alkynylthio, each cycloalkyl, alkenyl or alkynyl being a lower radical;
  amino, alkylamino, dialkylamino or acylamino, each alkyl being a lower radical;
  lower alkoxycarbonyl;
  N-alkylcarbamoyl, N,N-dialkylcarbamoyl, N-alkylsulfamoyl or N,N-dialkylsulfamoyl, each alkyl being a lower radical;
$R_1$ and $R_2$ are, independently, hydrogen, alkyl, haloalkyl, cycloalkyl, halocycloalkyl, cyano, alkoxyalkyl or alkoxycarbonyl, or $R_1$ and $R_2$ together form alkylene, each alkyl, cycloalkyl, alkoxy or alkylene being a lower radical;
$R_3$ is hydrogen, alkyl, haloalkyl, cycloalkyl, halocycloalkyl, alkenyl, alkynyl, alkoxyalkyl, alkylthioalkyl, cyanoalkyl, haloalkoxyalkyl, dialkylaminoalkyl, phenyl or benzyl, each alkyl, cycloalkyl, alkoxy, alkenyl or alkynyl being a lower radical;
W is an oxygen or sulfur atom, SO or $SO_2$;
$R_5$ is lower alkyl;
$R_6$ and $R_7$ are, independently, hydrogen or lower alkyl; and the adjective "lower" means a group having up to 6 carbon atoms.
2. A compound according to claim 1, wherein $R_5$ is methyl, $R_6$ is methyl and $R_7$ is hydrogen.
3. A compound according to claim 1, having at least one feature selected from the group consisting of:
  (a) $R_3$ is hydrogen, lower alkyl or lower cycloalkyl;
  (b) $R_1$ is hydrogen, lower alkyl, lower cycloalkyl, cyano, lower alkoxycarbonyl or lower haloalkyl;
  (c) $R_2$ is hydrogen or methyl;
  (d) $X_3$ is H; and
  (e) $X_1$ or $X_2$ is lower alkyl, cyano, halogen, lower haloalkyl, lower alkoxy or lower haloalkoxy.
4. A compound according to claim 3, wherein $R_5$ is methyl, $R_6$ is methyl and $R_7$ is hydrogen.
5. A compound according to claim 1, wherein both double bonds in formula (I) as shown in claim 1 have the E configuration.
6. A compound according to claim 5, wherein $R_5$ is methyl, $R_6$ is methyl and $R_7$ is hydrogen.
7. A compound according to claim 5, having at least one feature selected from the group consisting of:
  (a) $R_3$ is hydrogen, lower alkyl or lower cycloalkyl;
  (b) $R_1$ is hydrogen, lower alkyl, lower cycloalkyl, cyano, lower alkoxycarbonyl or lower haloalkyl;
  (c) $R_2$ is hydrogen or methyl;
  (d) $X_3$ is H; and
  (e) $X_1$ or $X_2$ is lower alkyl, cyano, halogen, lower haloalkyl, lower alkoxy or lower haloalkoxy.
8. A compound according to claim 7, wherein $R_5$ is methyl, $R_6$ is methyl and $R_7$ is hydrogen.
9. A compound according to claim 1, wherein $X_1$ is methyl or hydrogen; $X_2$ and $X_3$ are hydrogen; $R_1$ is hydrogen or methyl; $R_2$ is hydrogen; $R_3$ is hydrogen or lower alkyl; and W is an oxygen atom.
10. A compound according to claim 9, wherein $R_5$ is methyl, $R_6$ is methyl and $R_7$ is hydrogen.
11. The compound according to claim 1, wherein:
  (a) G is $G_3$, $R_1$ is H, $R_2$ is H, $X_1$ is H, $X_2$ is H, $X_3$ is H, $R_3$ is H, W is O, $R_5$ is $CH_3$, $R_6$ is $CH_3$ and $R_7$ is H;
  (b) G is $G_3$, $R_1$ is H, $R_2$ is H, $X_1$ is H, $X_2$ is H, $X_3$ is H, $R_3$ is $CH_2CH_3$, W is O, $R_5$ is $CH_3$, $R_6$ is $CH_3$ and $R_7$ is H;
  (c) G is $G_3$, $R_1$ is H, $R_2$ is H, $X_1$ is 2-Cl, $X_2$ is H, $X_3$ is H, $R_3$ is $CH_3$, W is O, $R_5$ is $CH_3$, $R_6$ is $CH_3$ and $R_7$ is H;
  (d) G is $G_3$, $R_1$ is H, $R_2$ is H, $X_1$ is 2-$OCH_3$, $X_2$ is H, $X_3$ is H, $R_3$ is $CH_3$, W is O, $R_5$ is $CH_3$, $R_6$ is $CH_3$ and $R_7$ is H;
  (e) G is $G_3$, $R_1$ is H, $R_2$ is H, $X_1$ is H, $X_2$ is 4-$CH_3$, $X_3$ is H, $R_3$ is $CH_3$, W is O, $R_5$ is $CH_3$, $R_6$ is $CH_3$ and $R_7$ is H; or
  (f) G is $G_3$, $R_1$ is H, $R_2$ is H, $X_1$ is H, $X_2$ is H, $X_3$ is H, $R_3$ is $CH_2CH_3$, W is S, $R_5$ is $CH_3$, $R_6$ is $CH_3$ and $R_7$ is H.
12. A process for the preparation of a compound according to claim 1, which comprises reacting a compound having the formula (II):

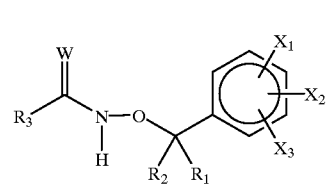

with a compound having the formula (III):

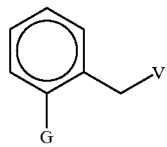

wherein $R_1$, $R_2$, $R_3$, W, $X_1$, $X_2$, $X_3$ and G are as defined in claim 1 and V is a halogen atom.

13. A process according to claim 12, wherein the reaction is conducted in the presence of an acid binding agent.

14. A process according to claim 13, wherein the reaction is conducted in the presence of a solvent.

15. A process according to claim 13, wherein the reaction is conducted at a temperature from −80° C. to 150° C.

16. A process according to claim 14, wherein the reaction is conducted at a temperature from −80° C. to 150° C. or to the boiling point of the solvent.

17. A process according to claim 13, wherein the relative amount of compound of formula (III) to compound of formula (II) is from 0.5 to 2.

18. A process according to claim 17, wherein the relative amount of compound of formula (III) to compound of formula (II) is from 0.9 to 1.1.

19. A process according to claim 12, wherein the product has the Z stereochemistry on the hydroximic moiety and wherein said process further comprises heating said product in a solvent to afford the corresponding E isomer of formula (I).

20. A process according to claim 19, wherein the reaction is conducted under UV irradiation.

21. A process according to claim 19, wherein the reaction is conducted in the presence of an acid catalyst.

22. A process according to claim 20, wherein the reaction is conducted in the presence of an acid catalyst.

23. A process according to claim 12, wherein in the product W is S, and wherein said process further comprises oxidizing said product with an oxidizing agent in an inert solvent to afford the corresponding compound of formula (I) wherein W is SO or $SO_2$.

24. A process for the preparation of a compound according to claim 1 wherein $R_6$ is methyl and $R_7$ is hydrogen, which comprises reacting a compound having the formula (I-1):

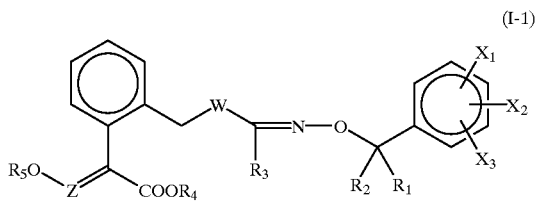

wherein $R_1$, $R_2$, $R_3$, W, $X_1$, $X_2$, $X_3$ and $R_5$ are as defined in claim 1, $R_4$ is lower alkyl and Z is N or CH, with methylamine.

25. A process according to claim 24, wherein the reaction is conducted at a temperature from −50° C. to 100° C.

26. A process according to claim 24, wherein the reaction is conducted in the presence of a solvent.

27. A process according to claim 26, wherein the reaction is conducted at a temperature from −50° C. to the boiling point of the solvent.

28. A process according to claim 24, wherein the molar ratio of methylamine to compound of formula (I-1) is from 1 to 5.

29. A process according to claim 28, wherein the molar ratio of methylamine to compound of formula (I-1) is from 1.1 to 2.

30. A process according to claim 24, wherein in the product W is S, and wherein said process further comprises oxidizing said product with an oxidizing agent in an inert solvent to afford the corresponding compound of formula (I) wherein W is SO or $SO_2$.

31. A pesticidal composition comprising a pesticidally effective amount of a compound of formula (I) as claimed in claim 1 and at least one member selected from the group consisting of an agriculturally acceptable solid or liquid carrier and an agriculturally acceptable surface-active agent.

32. A composition according to claim 31, wherein the pesticidally effective amount of compound of formula (I) is a fungicidally effective amount, said composition comprising from 0.1 to 99% w/w of compound of formula (I).

33. A composition according to claim 32, said composition comprising from 1 to 60% w/w of compound of formula (I).

34. A process for the prevention or treatment of fungal disease in cultivated plants, said process comprising applying to said plants or to the locus in which they grow a fungicidally effective amount of a compound as claimed in claim 1.

35. A process according to claim 34, wherein the compound of formula (I) is applied to the foliage, the dose is from 1 to 10,000 ppm and the application rate is from 5 g/ha to 10 kg/ha.

36. A process according to claim 35, wherein the dose is from 1 to 500 ppm.

37. A process according to claim 35, wherein the application rate is from 10 g/ha to 1 kg/ha.

38. A process according to claim 36, wherein the application rate is from 10 g/ha to 1 kg/ha.

39. A process according to claim 37, wherein the application rate is from 50 g/ha to 500 g/ha.

40. A process according to claim 38, wherein the application rate is from 50 g/ha to 500 g/ha.

41. A process according to claim 34, wherein the compound of formula (I) is applied to the soil and the application rate is from 0.01 kg/ha to 100 kg/ha.

42. A process according to claim 41, wherein the application rate is from 0.01 kg/ha to 2 kg/ha.

43. A process according to claim 34, wherein said plants are cereals.

44. A process according to claim 35, wherein said plants are cereals.

* * * * *